United States Patent
Bae et al.

(10) Patent No.: US 10,572,637 B2
(45) Date of Patent: Feb. 25, 2020

(54) USER AUTHENTICATION METHOD AND APPARATUS BASED ON ELECTROCARDIOGRAM (ECG) SIGNAL

(71) Applicant: Samsung Electronics Co., Ltd., Suwon-si (KR)

(72) Inventors: Chisung Bae, Yongin-si (KR); Sang Joon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 292 days.

(21) Appl. No.: 14/755,971

(22) Filed: Jun. 30, 2015

(65) Prior Publication Data

US 2016/0063233 A1   Mar. 3, 2016

(30) Foreign Application Priority Data

Sep. 1, 2014  (KR) .................. 10-2014-0115511

(51) Int. Cl.
*G06F 21/32* (2013.01)
*H04L 9/32* (2006.01)
(Continued)

(52) U.S. Cl.
CPC .......... *G06F 21/32* (2013.01); *A61B 5/04012* (2013.01); *A61B 5/0456* (2013.01);
(Continued)

(58) Field of Classification Search
CPC .............................. G06F 21/32; H04L 9/3231
See application file for complete search history.

(56) References Cited

U.S. PATENT DOCUMENTS

| 6,827,695 B2 | 12/2004 | Palazzolo et al. |
| 7,071,817 B2 | 7/2006 | Haselsteiner et al. |

(Continued)

FOREIGN PATENT DOCUMENTS

| CN | 101773394 A | 7/2010 |
| CN | 103345600 A | 10/2013 |

(Continued)

OTHER PUBLICATIONS

R Sameni et. al., "Filtering Noisy ECG Signals Using the Extended Kalman Filter Based on a Modified Dynamic ECG Model", date: 2005; pp. 1017 to 1020; url: http://www.cinc.org/archives/2005/pdf/1017.pdf (Year: 2005).*

(Continued)

*Primary Examiner* — Maung T Lwin
*Assistant Examiner* — Suman Debnath
(74) *Attorney, Agent, or Firm* — NSIP Law

(57) ABSTRACT

A user authentication apparatus includes an electrocardiogram (ECG) waveform acquirer configured to acquire an authentication ECG waveform of a user to authenticate the user; a filter configured to filter the authentication ECG waveform using a Kalman filter by applying a reference model parameter extracted from a reference ECG waveform to the Kalman filter; and an authenticator configured to compare the filtered ECG waveform and the reference ECG waveform, and determine whether the filtered authentication ECG waveform corresponds to the reference ECG waveform based on a result of the comparing.

24 Claims, 15 Drawing Sheets

(51) Int. Cl.
*A61B 5/00* (2006.01)
*H04L 29/06* (2006.01)
*A61B 5/0452* (2006.01)
*G07C 9/00* (2020.01)
*A61B 5/04* (2006.01)
*A61B 5/0456* (2006.01)

(52) U.S. Cl.
CPC .......... *A61B 5/04525* (2013.01); *A61B 5/725* (2013.01); *A61B 5/7246* (2013.01); *A61B 5/7264* (2013.01); *G07C 9/00158* (2013.01); *H04L 9/3231* (2013.01); *H04L 63/0861* (2013.01); *H04L 29/06809* (2013.01)

(56) References Cited

U.S. PATENT DOCUMENTS

| | | | |
|---|---|---|---|
| 7,647,185 B2 | 1/2010 | Tarassenko et al. | |
| 8,290,575 B2 | 10/2012 | Tarassenko et al. | |
| 8,483,809 B2 | 7/2013 | Kim et al. | |
| 9,235,657 B1* | 1/2016 | Wenzel | G05B 13/0265 |
| 2006/0189924 A1 | 8/2006 | Blakley et al. | |
| 2006/0293606 A1 | 12/2006 | Tomita | |
| 2007/0123779 A1* | 5/2007 | Hoctor | A61B 5/02125 600/438 |
| 2008/0082018 A1 | 4/2008 | Sackner et al. | |
| 2011/0118969 A1 | 5/2011 | Krishnaswamy | |
| 2011/0301436 A1 | 12/2011 | Teixeira | |
| 2012/0123232 A1* | 5/2012 | Najarian | A61B 5/0022 600/345 |
| 2015/0028996 A1* | 1/2015 | Agrafioti | G06F 21/40 340/5.82 |

FOREIGN PATENT DOCUMENTS

| | | | |
|---|---|---|---|
| CN | 103714281 A | 4/2014 | |
| JP | 4257538 B2 | 2/2009 | |
| KR | 10-1002020 B1 | 12/2010 | |
| KR | 10-2013-0032078 A | 4/2013 | |
| WO | WO 03/000015 A2 | 1/2003 | |
| WO | WO 2009/127799 A1 | 10/2009 | |
| WO | WO 2010/077997 A2 | 7/2010 | |
| WO | WO 2012/151680 A1 | 11/2012 | |
| WO | WO 2013/052944 A1 | 4/2013 | |

OTHER PUBLICATIONS

R. Sameni et al., "A Nonlinear Bayesian Filtering Framework for ECG Denoising," *IEEE Transactions on Biomedical Engineering*, vol. 54, No. 12, Dec. 2007, pp. 2172-2185.

F. Sufi et al., "ECG-Based Authentication," Chapter 17 in *Handbook of Information and Communication Security*, P. Stavroulakis et al. (editors), 2010, pp. 309-331, Heidelberg, New York, Springer.

Israel, et al., "ECG to identify individuals.", *Pattern recognition*, vol. 38.1, 2005, pp. 133-142.

Chan, et al., "Wavelet Distance Measure for Person Identification Using Electrocardiograms," *IEEE Transactions on Instrumentation and Measurement*, vol. 57, No. 2, Feb. 2008:, pp. 248-253.

Ting, et al. "ECG based personal identification using extended kalman filter," *Information Sciences Signal Processing and their Applications (ISSPA)*, 2010 10th International Conference on. IEEE, May 2010, pp. 774-777.

Naraghi, et al. "Human identification using ECG feature extracted from innovation signal of Extended Kalman Filter," *Biomedical Engineering and Informatics (BMEI)*, 2012 5th International Conference on., Oct. 2012, pp. 545-549.

Tantawi, et al. "Fiducial feature reduction analysis for electrocardiogram (ECG) based biometric recognition," *Journal of Intelligent Information Systems*, vol. 40 No. 1, 2013, pp. 17-39.

European Search Report dated Jan. 26, 2016, in counterpart European Application No. 15170931.8 (11 Pages in English).

Chinese Office Action dated Oct. 26, 2018 in Chinese Patent Application No. 201510231072.1 (27 pages in English, 13 pages in Chinese).

* cited by examiner

USER AUTHENTICATION METHOD AND APPARATUS BASED ON ELECTROCARDIOGRAM (ECG) SIGNAL

CROSS-REFERENCE TO RELATED APPLICATIONS

This application claims the benefit under 35 USC 119(a) of Korean Patent Application No. 10-2014-0115511 filed on Sep. 1, 2014, in the Korean Intellectual Property Office, the entire disclosure of which is incorporated herein by reference for all purposes.

BACKGROUND

1. Field

The following description relates to a user authentication method and apparatus based on an electrocardiogram (ECG) signal.

2. Description of Related Art

Technology for applying signals and data extracted from a body to various systems is developing. For example, biometric technology for establishing a security system based on a biosignal and biometric data is drawing attention. The biometric technology may be technology for extracting a signal or data associated with a body of a user and comparing a result of the extracting to pre-stored data, thereby authenticating the user as a registered user through identification. As one example, technology for recognizing a user based on a personal electrocardiogram (ECG) signal is under development in a biometric technology field.

The biometric technology uses a unique biosignal of each user. Since the unique biosignal cannot be stolen or lost and has robustness against forgery or falsification, the biometric technology is highly favored in a security field. Recently, research is being conducted to improve a unique biosignal recognition rate.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a user authentication apparatus includes an electrocardiogram (ECG) waveform acquirer configured to acquire an authentication ECG waveform of a user to be authenticated; a filter configured to filter the authentication ECG waveform using a Kalman filter by applying a reference model parameter extracted from a reference ECG waveform to the Kalman filter; and an authenticator configured to compare the filtered authentication ECG waveform and the reference ECG waveform, and determine whether the filtered authentication ECG waveform corresponds to the reference ECG waveform based on a result of the comparing.

The authentication ECG waveform may include a plurality of ECG waveforms; and the apparatus further may include an ECG waveform extractor configured to align the plurality of ECG waveforms included in the authentication ECG waveform based on an R peak.

The reference model parameter may include any one or any combination of a first amplitude parameter indicating an amplitude for each of a plurality of first Gaussian functions extracted from the reference ECG waveform, a first duration parameter indicating a duration for each of the first Gaussian functions, a first position parameter indicating a position for each of the first Gaussian functions, and a first angular velocity parameter indicating an angular velocity based on a change in a phase of the reference ECG waveform.

The filter may be further configured to extract a predicted authentication ECG waveform by applying the reference model parameter to the authentication ECG waveform using the Kalman filter, and output the filtered authentication ECG waveform by combining the authentication ECG waveform and the predicted authentication ECG waveform.

The apparatus may further include a feature point extractor configured to extract a plurality of feature points from the filtered authentication ECG waveform.

The feature point extractor may be further configured to extract a plurality of second Gaussian functions from the filtered authentication ECG waveform, and extract any one or any combination of a second amplitude parameter indicating an amplitude for each of the second Gaussian functions, a second duration parameter indicating a duration for each of the second Gaussian functions, and a second position parameter indicating a position for each of the second Gaussian functions so that a distance between the filtered authentication ECG waveform and a sum of the second Gaussian functions is minimized.

The authenticator may be further configured to extract a similarity between the filtered authentication ECG waveform and the reference ECG waveform, and determine whether the filtered authentication ECG waveform corresponds to the reference ECG waveform based on the similarity.

The authenticator may be further configured to extract the similarity between a plurality of feature points in the filtered authentication ECG waveform and a plurality of feature points in the reference ECG waveform, and determine whether the filtered authentication ECG waveform corresponds to the reference ECG waveform based on the similarity.

The authenticator may be further configured to determine the similarity based on any one or any combination of a distance between the first amplitude parameter and the second amplitude parameter, a distance between the first duration parameter and the second duration parameter, and a distance between the first position parameter and the second position parameter.

The authenticator may be further configured to determine the similarity by applying a weight to each of the distance between the first amplitude parameter and the second amplitude parameter, the distance between the first duration parameter and the second duration parameter, and the distance between the first position parameter and the second position parameter.

The authenticator may be further configured to determine the filtered authentication ECG waveform as corresponding to the reference ECG waveform, and authenticate the user as being a user of the reference ECG waveform, in response to the similarity being greater than a predetermined threshold.

The filter, the feature point extractor, and the authenticator may be further configured to operate repetitively in response to the authenticator determining that the filtered authentication ECG waveform does not correspond to the reference ECG waveform.

The authenticator may be further configured to determine that the user is not the user of the reference ECG waveform in response to a number of operations repetitively performed by the filter, the feature point extractor, and the authenticator being greater than a predetermined threshold.

The authenticator may be further configured to authenticate the user as being the user of the reference ECG waveform in response to the similarity being greater than a predetermined threshold and increasing as the operations are repetitively performed by the filter, the feature point extractor, and the authenticator.

The feature point extractor may be further configured to extract as the feature points any one or any combination of a PR interval, a PR segment, a QRS complex, an ST segment, an ST interval, a QT interval, an RR interval, an amplitude, a position, a noise power, and a predetermined statistical value of the filtered authentication ECG waveform.

The authenticator may be further configured to authenticate the user by determining whether the user is a user of the reference ECG waveform based on a result of the comparing; and the filter may be further configured to reset a variable of the Kalman filter in response to the authenticator determining that the user is not the user of the reference ECG waveform.

In another general aspect, a user registration apparatus includes an electrocardiogram (ECG) waveform acquirer configured to acquire a registration ECG waveform of a user to register the user; an ECG waveform extractor configured to extract a representative ECG waveform from the registration ECG waveform based on an R peak; a model parameter extractor configured to extract a first model parameter by modeling the representative ECG waveform; a filter configured to filter the registration ECG waveform using a Kalman filter by applying the first model parameter to the Kalman filter; and a feature point extractor configured to extract a plurality of feature points from the filtered registration ECG waveform.

The model parameter extractor may be further configured to extract a plurality of first Gaussian functions from the representative ECG waveform, and extract any one or any combination of a first amplitude parameter indicating an amplitude for each of the first Gaussian functions, a first duration parameter indicating a duration for each of the first Gaussian functions, and a first position parameter for each of the first Gaussian functions so that a distance between the representative ECG waveform and a sum of the first Gaussian functions is minimized.

The filter may be further configured to extract a predicted registration ECG waveform by applying the first model parameter to the registration ECG waveform based on the first Gaussian functions using the Kalman filter, and output the filtered registration ECG waveform by combining the registration ECG waveform and the predicted registration ECG waveform.

The feature point extractor may be further configured to extract a plurality of second Gaussian functions from the filtered registration ECG waveform, and extract any one or any combination of a second amplitude parameter indicating an amplitude for each of the second Gaussian functions, a second duration parameter indicating a duration for each of the second Gaussian functions, and a second position parameter indicating a position for each of the second Gaussian functions so that a distance between the filtered registration ECG waveform and a sum of the second Gaussian functions is minimized.

The feature point extractor may be further configured to extract as the feature points any one or any combination of a PR interval, a PR segment, a QRS complex, an ST segment, an ST interval, a QT interval, an RR interval, an amplitude, a position, a noise power, and a predetermined statistic value of the filtered registration ECG waveform.

In another general aspect, a user authentication apparatus includes a register configured to extract a first model parameter by modeling a representative electrocardiogram (ECG) waveform extracted from a registration ECG waveform, filter the registration ECG waveform using a Kalman filter by applying the first model parameter to the Kalman filter, and extract a plurality of feature points from the filtered registration ECG waveform; and an authenticator configured to filter an authentication ECG waveform using the Kalman filter by applying a second model parameter included in the feature points to the Kalman filter, compare the filtered authentication ECG waveform and the filtered registration ECG waveform, and determine whether the filtered authentication ECG waveform corresponds to the registration ECG waveform based on a result of the comparing.

In another general aspect, a user authentication method includes acquiring an authentication electrocardiogram (ECG) waveform of a user to be authenticated; filtering the authentication ECG waveform using a Kalman filter by applying a reference model parameter extracted from a reference ECG waveform to the Kalman filter; comparing the filtered authentication ECG waveform and the reference ECG waveform; and determining whether the filtered authentication ECG waveform corresponds to the reference ECG waveform based on a result of the comparing.

In another general aspect, a user registration method includes acquiring a registration electrocardiogram (ECG) waveform of a user to be authenticated; extracting a representative ECG waveform from the registration ECG waveform based on an R peak; extracting a model parameter by modeling the representative ECG waveform; filtering the registration ECG waveform using a Kalman filter by applying the model parameter to the Kalman filter; and extracting a plurality of feature points from the filtered registration ECG waveform.

In another general aspect, a user authentication method includes extracting a first model parameter by modeling a representative electrocardiogram (ECG) waveform extracted from a registration ECG waveform; filtering the registration ECG waveform using a Kalman filter by applying the first model parameter to the Kalman filter; extracting a plurality of feature points from the filtered registration ECG waveform; filtering an authentication ECG waveform using the Kalman filter by applying a second model parameter included in the feature points to the Kalman filter; comparing the filtered authentication ECG waveform and the filtered registration ECG waveform; and determining whether the filtered authentication ECG waveform corresponds to the filtered registration ECG waveform based on a result of the comparing.

In another general aspect, a user authentication method includes acquiring an authentication electrocardiogram (ECG) waveform of a user to be authenticated; filtering the authentication ECG waveform using a predictive filter adjusted based on a characteristic extracted from a reference ECG waveform of a pre-registered user; comparing the filtered authentication ECG waveform and the reference ECG waveform; and determining whether the user is the pre-registered user based on a result of the comparing.

The characteristic may be a parameter of a Gaussian function modeling the reference ECG waveform.

The method may further include extracting a plurality of first feature points from the filtered authentication ECG waveform; and extracting a plurality of second feature points from the reference ECG waveform; and the comparing may include comparing the plurality of first feature points and the plurality of second feature points.

Other features and aspects will be apparent from the following detailed description, the drawings, and the claims.

DETAILED DESCRIPTION

Figure 1:
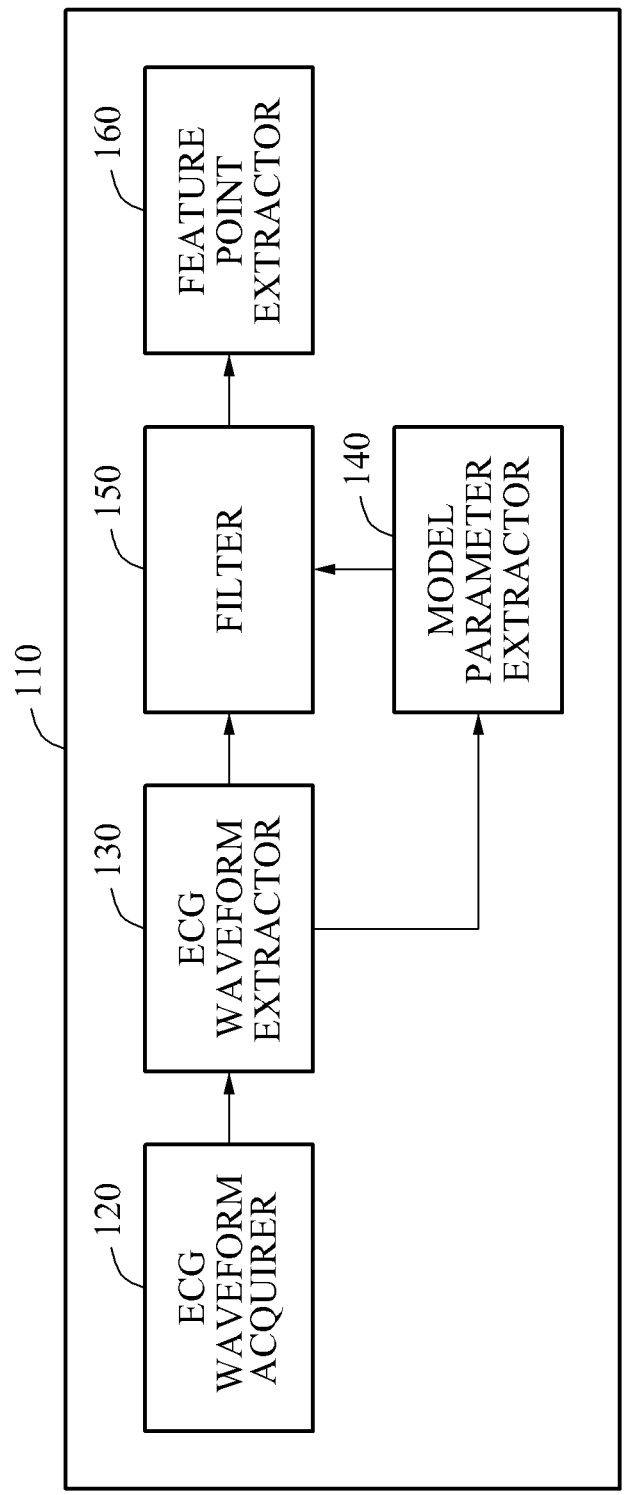
FIG. 1 illustrates an example of a user registration apparatus.

The following detailed description is provided to assist the reader in gaining a comprehensive understanding of the methods, apparatuses, and/or systems described herein. However, various changes, modifications, and equivalents of the methods, apparatuses, and/or methods described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The terminology used herein is for the purpose of describing particular examples only, and is not intended to limit the scope of the disclosure in any way. As used herein, the singular forms "a," "an," and "the" are intended to include the plural forms as well, unless the context clearly indicates otherwise. It will be further understood that the terms "comprise," "comprises," "comprising," "includes," "include," "including," "have," "has," and "having," when used in this application, specify the presence of stated features, numbers, operations, elements, components, or combinations thereof, but do not preclude the presence or addition of one or more other features, numbers, operations, elements, components, or combinations thereof.

Unless otherwise defined, all terms including technical and scientific terms, used herein have the same meaning as commonly understood by one of ordinary skill in the art to which this application pertains. It will be further understood that terms, such as those defined in commonly used dictionaries, should be interpreted as having a meaning that is consistent with their meaning in the context of the relevant art, and are not to be interpreted in an idealized or overly formal sense unless expressly so defined herein.

FIG. 1 illustrates an example of a user registration apparatus 110.

Referring to FIG. 1, the user registration apparatus 110 includes an electrocardiogram (ECG) waveform acquirer 120, an ECG waveform extractor 130, a model parameter extractor 140, a filter 150, and a feature point extractor 160. The user registration apparatus 110 registers an ECG signal of a user. As described with reference to FIG. 2, a user authentication apparatus 210 authenticates a user by comparing ECG information acquired for an authentication and ECG information registered in the user registration apparatus 110 in advance. In one example, although the user registration apparatus 110 is described as being separate from the user authentication apparatus 210 of FIG. 2, the user registration apparatus 110 and the user authentication apparatus 210 may be configured in a single apparatus or may be separate from one another.

The ECG waveform acquirer 120 acquires an ECG waveform of a user using an ECG sensor to register the user. In one example, the ECG waveform acquirer 120 stores ECG signals for a plurality of users. Hereinafter, the ECG waveform used to register the user may also be referred to as a registration ECG waveform.

The ECG sensor includes a plurality of electrodes, an amplifier, and a digital filter. The electrodes sense the ECG signal of the user through a contact with, for example, a finger skin of the user. The amplifier amplifies the ECG signal sensed by the electrodes. The amplifier may also be referred to as an analog front-end (AFE). The digital filter converts the amplified ECG signal into a digital signal. Through this process, a signal-to-noise ratio (SNR) of the ECG signal is improved.

The ECG waveform extractor 130 extracts a registration ECG waveform from the converted digital signal. In this example, the registration ECG waveform includes a plurality of ECG waveforms.

The ECG waveform extractor 130 extracts a representative ECG waveform from the registration ECG waveform based on an R peak of an ECG waveform. The ECG waveform has a variable time period and amplitude. For example, in an ECG waveform of the same user, a time period and amplitude may vary based on a respiration state of the user. Also, since the ECG waveform is acquired by sampling in the ECG sensor, a peak of the ECG waveform acquired in the ECG sensor may be different from a peak of an actual ECG waveform. Thus, the ECG waveform extractor 130 processes the ECG waveform into a form appropriate for the authentication. In one example, the ECG waveform extractor 130 performs preprocessing to remove dominant noise from the registration ECG waveform. As an example, during the preprocessing, the ECG waveform extractor 130 extracts a registration ECG waveform in a range from 0.5 to 40 hertz (Hz). Also, the ECG waveform extractor 130 eliminates the dominant noise such as a DC baseline wandering, a power noise, for example, an ECG waveform in a frequency band between 50 and 60 Hz, and a motion artifact from the registration ECG waveform.

Additionally, the ECG waveform extractor 130 aligns the plurality of ECG waveforms included in the registration ECG waveform based on the R peak. A P wave, a QRS wave, a T wave, and a U wave appear repetitively in the ECG waveform, and the R peak of the QRS wave has a greatest amplitude among these waves. Thus, the ECG waveform extractor 130 aligns the ECG waveform based on the R peak. The ECG waveform extractor 130 detects a plurality of R peaks from the registration ECG waveform, and aligns the plurality of ECG waveforms included in the registration ECG waveform based on the detected R peaks. Also, the ECG waveform extractor 130 extracts a representative ECG waveform from the ECG waveforms included in the registration ECG waveform. As an example, the ECG waveform extractor 130 extracts the representative ECG waveform by obtaining an average value of the ECG waveforms included in the registration ECG waveform.

The model parameter extractor 140 determines a standard deviation value and an average value of the representative ECG waveform, and extracts a plurality of Gaussian functions from the representative ECG waveform based on the standard deviation value and the average value of the representative ECG waveform. The model parameter extractor 140 models the representative ECG waveform based on the Gaussian functions using the following Equation 1.

$$\dot{\theta} = \omega \quad (1)$$
$$\dot{z} = -\sum_{i=1}^{N} \frac{\alpha_i \omega}{b_i^2} \Delta\theta_1 \exp\left(-\frac{\Delta\theta_i^2}{2b_i^2}\right)$$

In Equation 1, θ denotes a phase value of the ECG waveform and z denotes an amplitude of the ECG waveform at a corresponding phase. $\dot{\theta}$ and $\dot{z}$ denote values obtained by differentiating θ and z, respectively. ω denotes an angular velocity parameter indicating an angular velocity based on a change in a phase of the ECG waveform. The model parameter extractor 140 extracts an average heart rate of the user from the representative ECG waveform, and extracts the angular velocity parameter from the average heart rate. $\alpha_i$ denotes an amplitude parameter indicating an amplitude for each of the Gaussian functions, $b_i$ denotes a duration parameter indicating a duration for each of the Gaussian functions, and $\Delta\theta_i$ denotes a position parameter indicating a position for each for each of the Gaussian functions. In one example, model parameters include an amplitude parameter $\alpha_i$, a duration parameter $b_i$, a position parameter $\Delta\theta_i$, and an angular velocity parameter ω. The model parameters indicate unique characteristics of the user, and thus the model parameters will be different for each user.

The model parameter extractor 140 extracts the amplitude parameter $\alpha_i$, the duration parameter $b_i$, and the position parameter $\Delta\theta_i$ as model parameters using the following Equation 2.

$$\underset{\alpha_i, b_i, \Delta\theta_i}{\operatorname{argmin}} \|x - z\| \quad (2)$$

In Equation 2, x denotes the representative ECG waveform and z denotes a representative ECG waveform modeled using Equation 1. The modeled representative ECG waveform is a sum of the Gaussian functions. ∥ ∥ denotes a norm indicating a distance between x and z. The norm may be, for example, a Euclidean norm, an L1 norm, or a P norm, all of which are well known to one of ordinary skill in the art, and thus will not be described in detail here. The model parameter extractor 140 extracts the amplitude parameter $\alpha_i$, the duration parameter $b_i$, and the position parameter $\Delta\theta_i$ so that the modeled representative ECG waveform is closest to the representative ECG waveform, for example, so that a distance between the representative ECG waveform and the sum of the Gaussian functions is minimized.

The filter 150 filters the registration ECG waveform using a Kalman filter by applying the model parameters extracted by the model parameter extractor 140 to the Kalman filter. The Kalman filter may be, for example, an extended Kalman filter or an unscented Kalman filter, both of which are well known to one of ordinary skill in the art, and thus will not be described in detail here. As is well known to one of ordinary skill in the art, a Kalman filter is one type of predictive filter. Although the examples in this application describe the use of a Kalman filter, this is merely one example, and other types of predictive filters known to one of ordinary skill in the art may be used.

The filter 150 extracts a predicted registration ECG waveform by applying the amplitude parameter $\alpha_i$, the duration parameter $b_i$, the position parameter $\Delta\theta_i$, and the angular velocity parameter ω extracted by the model parameter extractor 140 to the registration ECG waveform using the Kalman filter. The filter 150 combines the registration ECG waveform extracted by the ECG waveform extractor 130 and the predicted registration ECG waveform in consideration of a statistical distribution of the registration ECG waveform extracted by the ECG waveform extractor 130 and the predicted registration ECG waveform using the Kalman filter. In one example, the filter 150 smooths the filtered registration waveform. For example, the filter 150 smooths the filtered registration ECG waveform using a fixed-lag smoother or a fixed-interval smoother, both of which are well known to one of ordinary skill in the art, and thus will not be described in detail here.

The feature point extractor 160 extracts a plurality of feature points from the filtered registration ECG waveform. In this example, the feature points include a PR interval, a PR segment, a QRS complex, an ST segment, an ST interval, a QT interval, and an RR interval of the filtered registration ECG waveform, an amplitude, a position, and a noise power of the filtered registration ECG waveform, or a statistical value and the model parameters of the filtered registration ECG waveform. In one example, the feature point extractor 160 determines a standard deviation value and an average value of the filtered registration ECG waveform, and extracts a plurality of Gaussian functions from the filtered registration ECG waveform based on the determined standard deviation value and average value. The feature point extractor 160 models the filtered registration ECG waveform using Equation 1 based on the Gaussian functions extracted from the filtered registration ECG waveform. Using the Equations 1 and 2, the feature point extractor 160 extracts an amplitude parameter, a duration parameter, and a position parameter so that a distance between the filtered registration ECG waveform and a sum of the Gaussian functions is minimized. The amplitude parameter indicates an amplitude for each of the Gaussian functions extracted from the filtered registration ECG waveform. The duration parameter indicates a duration for each of the Gaussian functions. The position parameter indicates a position for each of the Gaussian functions. Also, the feature point extractor 160 extracts an average heart rate of the user from the filtered registration ECG waveform, and extracts an angular velocity parameter from the average heart rate.

Figure 2:
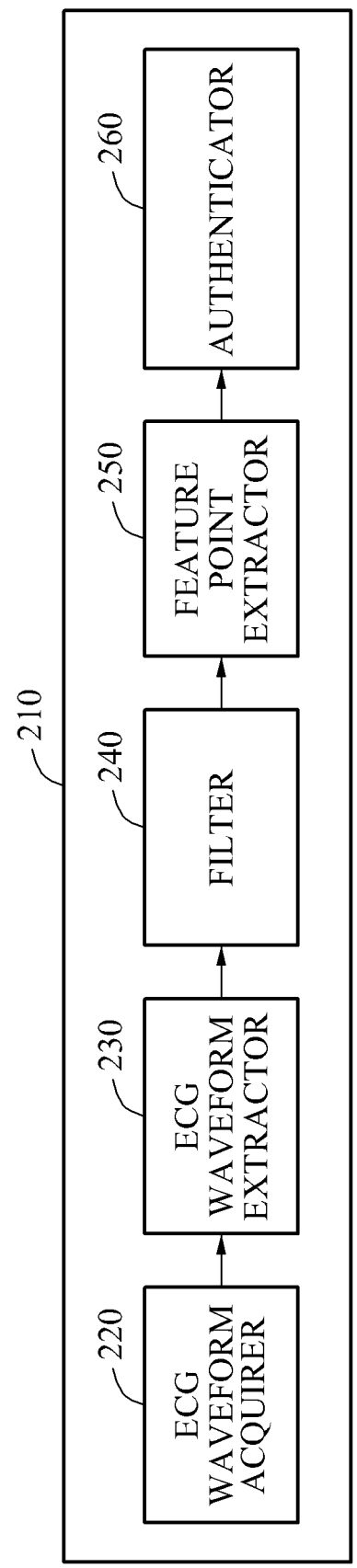
FIG. 2 illustrates an example of a user authentication apparatus.

FIG. 2 illustrates an example of the user authentication apparatus 210.

Referring to FIG. 2, the user authentication apparatus 210 includes an ECG waveform acquirer 220, an ECG waveform extractor 230, a filter 240, a feature point extractor 250, and an authenticator 260. The user authentication apparatus 210 authenticates whether a user corresponds to a pre-registered user by comparing ECG information acquired from the user and ECG information on the pre-registered user stored in the registration apparatus 110 of FIG. 1.

As described above, although the user authentication apparatus 210 is described as being separate from the user registration apparatus 110 of FIG. 1, the user registration apparatus 110 and the user authentication apparatus 210 may be configured in a single apparatus or may be separate from one another.

The ECG waveform acquirer 220 acquires an ECG waveform of a user using an ECG sensor. Hereinafter, an ECG waveform used to authenticate the user may also be referred to as an authentication ECG waveform.

The ECG sensor includes a plurality of electrodes, an amplifier, and a digital filter. The electrodes sense the ECG signal of the user through contact with, for example, a finger skin of the user. The amplifier amplifies the ECG signal sensed by the electrodes. The amplifier may also be referred to as an AFE. The digital filter converts the amplified ECG signal into a digital signal. Through this process, an SNR of the ECG signal is improved.

The ECG waveform extractor 230 extracts an authentication ECG waveform from the converted digital signal. In this example, the authentication ECG waveform includes a plurality of ECG waveforms.

The ECG waveform extractor 230 performs preprocessing to remove dominant noise from the authentication ECG waveform. As an example, during the preprocessing, the ECG waveform extractor 230 extracts an authentication ECG waveform in a range from 0.5 to 40 Hz. Also, the ECG waveform extractor 230 eliminates the dominant noise such as a DC baseline wandering, a power noise, for example, an ECG waveform in a frequency band between 50 and 60 Hz, and a motion artifact from the authentication ECG waveform.

Additionally, the ECG waveform extractor 230 aligns the plurality of ECG waveforms included in the authentication ECG waveform based on an R peak. The ECG waveform extractor 230 detects a plurality of R peaks from the authentication ECG waveform, and aligns the plurality of ECG waveforms included in the authentication ECG waveform based on the detected R peaks.

The filter 240 filters the authentication ECG waveform using a Kalman filter by applying a reference model parameter extracted from a reference ECG waveform to the Kalman filter. As is well known to one of ordinary skill in the art, a Kalman filter is one type of predictive filter. Although the examples in this application describe the use of a Kalman filter, this is merely one example, and other types of predictive filters known to one of ordinary skill in the art may be used. The reference ECG waveform is a registration ECG waveform of a pre-registered user, and the reference model parameter is a model parameter extracted based on the reference ECG waveform. The reference model parameter includes any one or any combination of an amplitude parameter indicating an amplitude for each of a plurality of Gaussian functions extracted from the reference ECG waveform, a duration parameter indicating a duration for each of the Gaussian functions, a position parameter indicating a position for each for each of the Gaussian functions, and an angular velocity parameter indicating an angular velocity based on a change in a phase of the reference ECG waveform. The reference model parameter is extracted from the reference ECG waveform using Equations 1 and 2. In one example, the filter 240 receives information on the reference ECG waveform and the reference model parameter from the user registration apparatus 110 of FIG. 1. The Kalman filter may be, for example, an extended Kalman filter or an unscented Kalman filter, both of which are well known to one of ordinary skill in the art, and thus will not be described in detail here.

The filter 240 extracts a predicted authentication ECG waveform by applying the reference model parameter to the authentication ECG waveform using the Kalman filter. The filter 240 combines the authentication ECG waveform extracted by the ECG waveform extractor 220 and the predicted authentication ECG waveform in consideration of a statistical distribution of the authentication ECG waveform extracted by the ECG waveform extractor 220 and the predicted authentication ECG waveform using the Kalman filter. The reference model parameter reflects unique characteristics of the reference ECG waveform. Accordingly, when the user of the authentication ECG waveform is the same as the user of the reference ECG waveform, a prediction error will be reduced in the Kalman filter, and thus the filtered authentication ECG waveform will be closer to the reference ECG waveform. When the user of the authentication ECG waveform is not the user of the reference ECG waveform, the prediction error will increase in the Kalman filter, and thus the filtered authentication ECG waveform will be farther from the reference ECG waveform and closer to the authentication ECG waveform.

In one example, the filter 240 smooths the filtered authentication ECG waveform. For example, the filter 240 smooths the filtered authentication ECG waveform using a fixed-lag smoother or a fixed-interval smoother, both of which are well known to one of ordinary skill in the art, and thus will not be described in detail here.

The feature point extractor 250 extracts a plurality of feature points from the filtered authentication ECG waveform. In this example, the feature points include any one or any combination of a PR interval, a PR segment, a QRS complex, an ST segment, an ST interval, a QT interval, and an RR interval of the filtered authentication ECG waveform, an amplitude, a position, and a noise power of the filtered authentication ECG waveform, and a statistical value and the model parameters of the filtered authentication ECG waveform.

In one example, the feature point extractor 250 determines a standard deviation value and an average value of the filtered authentication ECG waveform, and extracts a plurality of Gaussian functions. The feature point extractor 250 models the filtered authentication ECG waveform using Equation 1 based on the Gaussian functions extracted from the filtered authentication ECG waveform. The feature point extractor 250 extracts an amplitude parameter, a duration parameter, and a position parameter so that a distance between the filtered authentication ECG waveform and a sum of the Gaussian functions is minimized. The amplitude parameter indicates an amplitude for each of the Gaussian functions extracted from the filtered authentication ECG waveform. The duration parameter indicates a duration for each of the Gaussian functions. The position parameter indicates a position for each of the Gaussian functions. Also, the feature point extractor 250 extracts an average heart rate of the user from the filtered authentication ECG waveform, and extracts an angular velocity parameter from the average heart rate.

The authenticator 260 compares the filtered authentication ECG waveform and the reference ECG waveform and determines whether the filtered authentication ECG waveform corresponds to the reference ECG waveform. When the filtered authentication ECG waveform is determined to correspond to the reference ECG waveform, the authenticator 260 authenticates the user as being the user of the reference ECG waveform and allows the user to access an apparatus including the user authentication apparatus 210. When the filtered authentication ECG waveform is determined not to correspond to the reference ECG waveform, the authenticator 260 determines that the user is not the user of the reference ECG waveform and blocks the user from accessing the apparatus including the user authentication apparatus 210.

The authenticator 260 determines whether the filtered authentication ECG waveform corresponds to the reference ECG waveform based on a similarity between the filtered authentication ECG waveform and the reference ECG waveform. In one example, the authenticator 260 extracts the similarity based on a root mean square error (RMSE), a Euclidean distance, a cosine similarity, or a correlation between the filtered authentication ECG waveform and the reference ECG waveform, all of which are well known to one of ordinary skill in the art, and thus will not be described in detail here. In this example, the similarity increases according to an increase in the correlation or the cosine similarity, and may increases according to a decrease in the Euclidean distance or the RMSE.

Additionally, the authenticator 260 may extract the similarity between the filtered authentication ECG waveform and the reference ECG waveform using any scheme applicable to a comparison between the filtered authentication ECG waveform and the reference ECG waveform. In one example, the authenticator 260 extracts the similarity based on a distance between a plurality of feature points in the filtered authentication ECG waveform and a plurality of feature points in the reference ECG waveform. For example, the authenticator 260 may use a norm to obtain a similarity between the feature points of the filtered authentication ECG waveform and the feature points of the reference ECG waveform.

In one example, the authenticator 260 determines the similarity between the feature points of the filtered authentication ECG waveform and the feature points of the reference ECG waveform based on a distance between the model parameters extracted from the filtered authentication ECG waveform and the reference model parameters extracted from the reference ECG waveform as using the following Equation 3.

$$S(i, j)=\Sigma_{i=1}^{N}\{\rho_1 \cdot \|\alpha_i - \alpha_j\| + \rho_2 \cdot \|b_i - b_j\| + \rho_3 \cdot \|\Delta\theta_i - \Delta\theta_j\|\} \quad (3)$$

In Equation 3, $S(i, j)$ denotes a distance between the feature points of the filtered authentication ECG waveform and the feature points of the reference ECG waveform, $i$ denotes the reference ECG waveform, $j$ denotes the filtered authentication ECG waveform, and $N$ denotes a number of Gaussian functions. $\alpha_i$ denotes the amplitude parameter extracted from the reference ECG waveform, $\alpha_j$ denotes the amplitude parameter extracted from the filtered authentication ECG waveform, $b_i$ denotes the duration parameter extracted from the reference ECG waveform, $b_j$ denotes the duration parameter extracted from the filtered authentication ECG waveform, $\Delta\theta_i$ denotes the position parameter extracted from the reference ECG waveform, and $\Delta\theta_j$ denotes the position parameter extracted from the filtered authentication ECG waveform. $\rho_1$ denotes a first weight, $\rho_2$ denotes a second weight, and $\rho_3$ denotes a third weight. The authenticator 260 calculates a norm between $\alpha_i$ and $\alpha_j$, a norm between $b_i$ and $b_j$, and a norm between $\Delta\theta_i$ and $\Delta\theta_j$ for each of the Gaussian functions, and applies a different weight for each of the calculated norms. The norm may be, for example, a Euclidean norm, an L1 norm, or a P norm, all of which are well known to one of ordinary skill in the art, and thus will not be described in detail here. The authenticator 260 may set the first weight through the third weight based on a predetermined rule. In one example, a first weight $\rho_1$ may be relatively low due to an effect of a baseline wandering. Since the authentication ECG waveform is extracted by the ECG waveform extractor 230 based on the R peak, a second weight $\rho_2$ and a third weight $\rho_3$ may be relatively high. $S(i, j)$ denotes a distance between the authentication ECG waveform and the reference ECG waveform. The similarity may decrease according to an increase in a value of $S(i, j)$, and the similarity may increase according to a decrease in the value of $S(i, j)$. As one example, the authenticator 260 may use an inverse value of $S(i, j)$ as the similarity.

The authenticator 260 determines whether the filtered authentication ECG waveform corresponds to the reference ECG waveform based on the similarity. In one example, when the similarity is greater than a predetermined first threshold, the authenticator 260 determines that the filtered authentication ECG waveform corresponds to the reference ECG waveform, thereby authenticating the user as the user of the reference ECG waveform. When the authenticator 260 determines that the filtered authentication ECG waveform does not correspond to the reference ECG waveform, the user authentication apparatus 210 may repetitively perform operations of the filter 240, the feature point extractor 250, and the authenticator 260. In this example, when a number of operations repetitively performed by the filter 240, the feature point extractor 250, and the authenticator 260 is greater than a predetermined threshold, the authenticator 260 determines that the user is not the user of the reference ECG waveform. Also, when the similarity is greater than a predetermined second threshold, for example, a predetermined second threshold that is less than the first threshold, and the similarity increases as a result of the operations repetitively performed by the filter 240, the feature point extractor 250, and the authenticator 260, the authenticator 260 may authenticate the user as being the user of the reference ECG waveform.

In one example, when the authenticator 260 determines that the user is not the user of the reference ECG waveform, the filter 240 resets a variable of the Kalman filter. For example, when the authenticator determines that the user is not the user of the reference ECG waveform, the filter 240 initializes a covariance matrix and a state matrix of the Kalman filter. Conversely, when the user is authenticated as being the user of the reference ECG waveform, the filter 240 maintains the covariance matrix and the state matrix of the Kalman filter The covariance matrix and the state matrix of the Kalman filter are well known to one of ordinary skill in the art, and thus will not be described in detail here.

Through the operations of the ECG waveform acquirer 220, the ECG waveform extractor 230, the filter 240, the feature point extractor 250, and the authenticator 260, the user authentication apparatus 210 may accurately extract a feature point despite a low quality of an ECG waveform, and may reduce a false acceptance rate (FAR), a false rejection rate (FRR), and an amount of time used for the user authentication.

Figure 3:
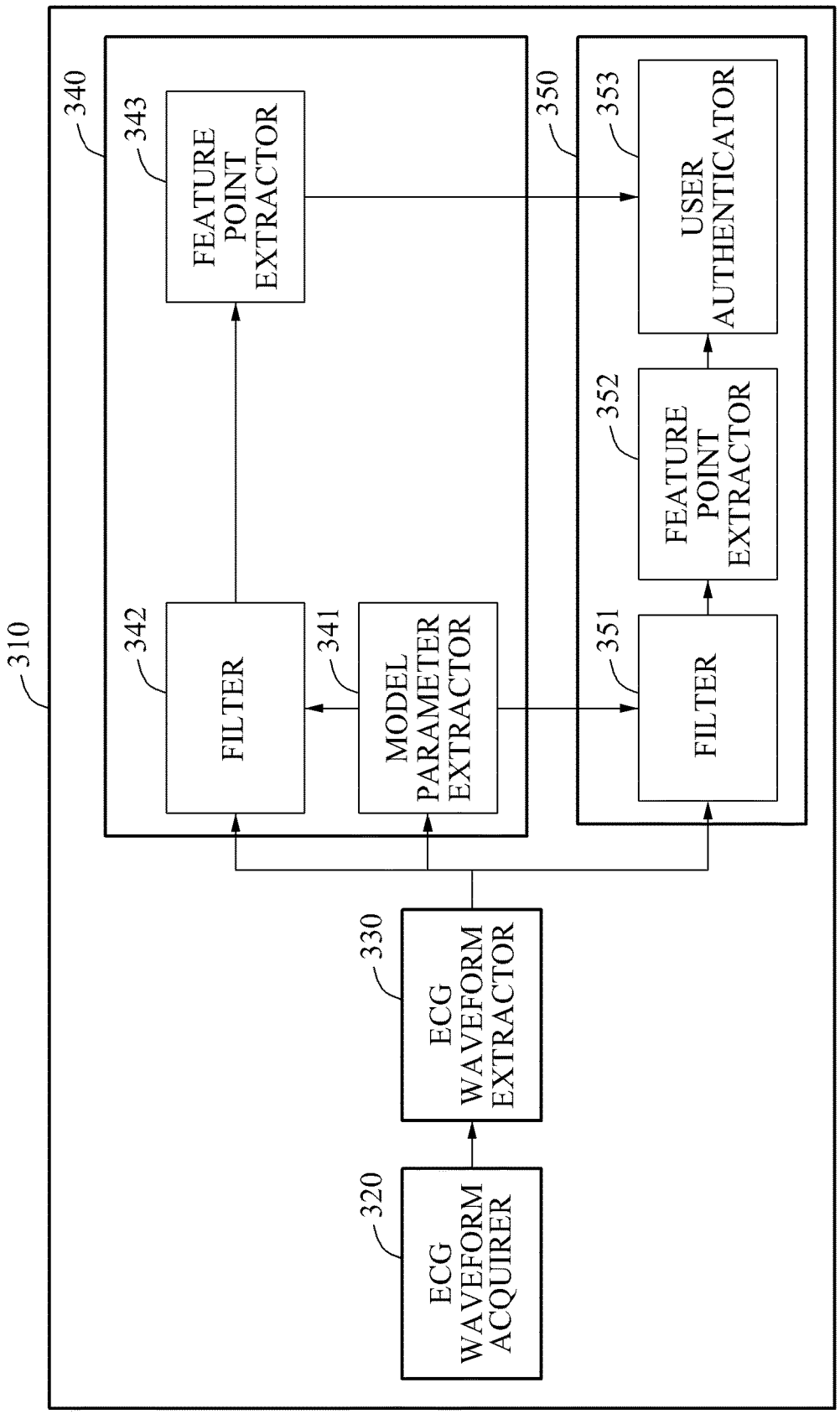
FIG. 3 illustrates another example of a user authentication apparatus.

FIG. 3 illustrates another example of a user authentication apparatus 310.

Referring to FIG. 3, the user authentication apparatus 310 includes an ECG waveform acquirer 320, an ECG waveform extractor 330, a register 340, and an authenticator 350.

The ECG waveform acquirer 320 acquires an ECG waveform of a user using an ECG sensor. The ECG sensor includes a plurality of electrodes, an amplifier, and a digital filter. The electrodes sense the ECG signal of the user through contact with, for example, a finger skin of the user. The amplifier amplifies the ECG signal sensed in the electrodes. The digital filter converts the amplified ECG signal into a digital signal.

The ECG waveform extractor 330 extracts an ECG waveform from the converted digital signal. In this example, the ECG waveform includes a plurality of ECG waveforms.

The ECG waveform extractor 330 performs preprocessing to remove dominant noise from the ECG waveform. As an example, during the preprocessing, the ECG waveform extractor 330 extracts an ECG waveform in a range from 0.5 to 40 Hz. Also, the ECG waveform extractor 330 eliminates the dominant noise such as a DC baseline wandering, a power noise, for example, an ECG waveform in a frequency band between 50 and 60 Hz, and a motion artifact from the ECG waveform.

Additionally, the ECG waveform extractor 330 aligns the plurality of ECG waveforms included in the ECG waveform based on an R peak. The ECG waveform extractor 330 detects a plurality of R peaks from the ECG waveform, and aligns the plurality of ECG waveforms included in the ECG waveform based on the detected R peaks.

In one example, the ECG waveform extractor 330 extracts a representative ECG waveform from the aligned ECG waveform. As an example, the ECG waveform extractor 330 extracts the representative ECG waveform by obtaining an average value of the aligned ECG waveform. The extracted representative ECG waveform is used in the register 340.

The register 340 registers the ECG waveform of the user. The register 340 includes a model parameter extractor 341, a filter 342, and a feature point extractor 343.

The model parameter extractor 341 determines a standard deviation value and an average value of the representative ECG waveform extracted by the ECG waveform extractor 330, and extracts a plurality of Gaussian functions from the representative ECG waveform based on the standard deviation value and the average value. Based on the Gaussian functions, the model parameter extractor 341 models the representative ECG waveform using Equation 1 and extracts an amplitude parameter, a duration parameter, and a position parameter as model parameters using Equation 2. Also, the model parameter extractor 341 extracts an average heart rate of the user from the representative ECG waveform, and extracts an angular velocity parameter corresponding to the model parameter from the average heart rate.

The filter 342 filters a registration ECG waveform using a Kalman filter by applying the model parameters extracted by the model parameter extractor 341 to the Kalman filter.

The filter 342 predicts an ECG waveform by applying the amplitude parameter, the duration parameter, the position parameter, and the angular velocity parameter extracted by the model parameter extractor 341 to the representative ECG waveform using the Kalman filter. As is well known to one of ordinary skill in the art, a Kalman filter is one type of predictive filter. Although the examples in this application describe the use of a Kalman filter, this is merely one example, and other types of predictive filters known to one of ordinary skill in the art may be used. The filter 342 combines the registration ECG waveform and the predicted representative ECG waveform by applying different weights to the registration ECG waveform and the predicted representative ECG waveform, and extracts an ECG waveform having a least RMSE with respect to the representative ECG waveform, thereby providing a result of the extracting as a filtered registration ECG waveform. RMSE is well known to one of ordinary skill in the art, and thus will not be described in detail here. Also, the filter 342 smooths the filtered registration ECG waveform.

The feature point extractor 343 extracts a plurality of feature points from the filtered registration ECG waveform. The feature point extractor 343 extracts any one or any combination of a PR interval, a PR segment, a QRS complex, an ST segment, an ST interval, a QT interval, and an RR interval of the filtered registration ECG waveform, an amplitude, a position, and a noise power of the filtered representative ECG waveform, and a predetermined statistical value of the filtered representative ECG waveform. Also, the feature point extractor 343 extracts model parameters of the filtered registration ECG waveform. In this example, the feature point extractor 343 determines a standard deviation value and an average value of the filtered registration ECG waveform, and extracts a plurality of Gaussian functions from the filtered registration ECG waveform based on the standard deviation value and the average value. Using Equations 1 and 2, the feature point extractor 343 may extract an amplitude parameter, a duration parameter, and a position parameter from the filtered registration ECG waveform. Also, the feature point extractor 343 may extract an average heart rate of the user from the filtered registration ECG waveform, and extract an angular velocity parameter based on the average heart rate.

The authenticator 350 authenticates whether a user attempting to be authenticated is a pre-registered user based on ECG information on the user attempting to be authenticated and ECG information on the pre-registered user stored in the register 340. The authenticator 350 includes a filter 351, a feature point extractor 352, and a user authenticator 353.

The filter 351 filters an authentication ECG waveform of the user attempting to be authenticated using the Kalman filter by applying the reference model parameter indicating the model parameter extracted by the model parameter extractor 341 to the Kalman filter.

The filter 351 applies the Kalman filter to the authentication ECG waveform. The Kalman filter may be used to extract a predicted authentication ECG waveform by applying the reference model parameter to the authentication ECG waveform. The filter 351 outputs a filtered authentication ECG waveform by applying a different weight for each of the authentication ECG waveform and a predicted target ECG waveform. Also, the filter 351 smooths the filtered authentication ECG waveform.

The feature point extractor 352 extracts a plurality of feature points from the filtered authentication ECG waveform. The feature point extractor 352 extracts any one or any combination of a PR interval, a PR segment, a QRS complex, an ST segment, an ST interval, a QT interval, and an RR interval of the filtered authentication ECG waveform, an amplitude, a position, and a noise power of the filtered authentication ECG waveform, and a statistical value and the model parameter of the filtered authentication ECG waveform. Also, the feature point extractor 352 may extract the model parameter from the filtered authentication ECG waveform. In this example, the feature point extractor 352 determines a standard deviation value and an average value of the filtered authentication ECG waveform, and extracts a plurality of Gaussian functions from the filtered authentication ECG waveform based on the standard deviation value and the average value. Using Equations 1 and 2, the feature point extractor 352 extracts an amplitude parameter, a duration parameter, and a position parameter from the filtered authentication ECG waveform. Also, the feature point extractor 352 extracts an average heart rate of the user from the filtered authentication ECG waveform, and extracts an angular velocity parameter based on the average heart rate.

The user authenticator 353 compares the filtered authentication ECG waveform and the filtered registration ECG waveform, and determines whether the filtered authentication ECG waveform corresponds to the filtered registration ECG waveform.

The user authenticator 353 determines whether the filtered authentication ECG waveform corresponds to the filtered registration ECG waveform based on a similarity between the filtered authentication ECG waveform and the filtered registration ECG waveform. In one example, the user authenticator 353 extracts the similarity based on an RMSE, a Euclidean distance, a cosine similarity, or a correlation between the filtered authentication ECG waveform and the filtered registration ECG waveform, all of which are well known to one of ordinary skill in the art, and thus will not be described in detail here. The similarity increases as the correlation or the cosine similarity increases, and increases as the Euclidean distance or the RMSE decreases.

Additionally, the user authenticator 353 may extract the similarity between the filtered authentication ECG waveform and the filtered registration ECG waveform using any scheme applicable to a comparison between the filtered authentication ECG waveform and the filtered registration ECG waveform. In one example, the user authenticator 353 extracts the similarity based on a distance between a plurality of feature points in the filtered authentication ECG waveform and a plurality of feature points in the filtered registration ECG waveform. Also, the user authenticator 353 may determine the similarity between the feature points of the filtered authentication ECG waveform and the feature points of the filtered registration ECG waveform based on a distance between the model parameters extracted from the filtered authentication ECG waveform and the reference model parameters extracted from the filtered registration ECG waveform as shown in Equation 3.

The user authenticator 353 determines whether the filtered authentication ECG waveform corresponds to the filtered registration ECG waveform based on the similarity. In one example, when the similarity is greater than a predetermined first threshold, the user authenticator 353 determines the filtered authentication ECG waveform as corresponding to the filtered registration ECG waveform, thereby authenticating the user as being the user of the registration ECG waveform. When the authenticator 353 determines that the filtered authentication ECG waveform does not correspond to the filtered registration ECG waveform, the user authentication apparatus 310 may repetitively perform operations of the ECG waveform extractor 330, the filter 351, the feature point extractor 352, and the user authenticator 353. In this example, when a number of operations repetitively performed by the ECG waveform extractor 330, the filter 351, the feature point extractor 352, and the user authenticator 353 is greater than a predetermined threshold, the user authenticator 353 determines that the user is not the user of the registration ECG waveform. Also, when the similarity is greater than a predetermined second threshold, and when the similarity increases through the operations repetitively performed by the ECG waveform extractor 330, the filter 351, the feature point extractor 352, and the user authenticator 353, the user authenticator 353 authenticates the user as being the same as the user of the reference ECG waveform.

Figure 4:
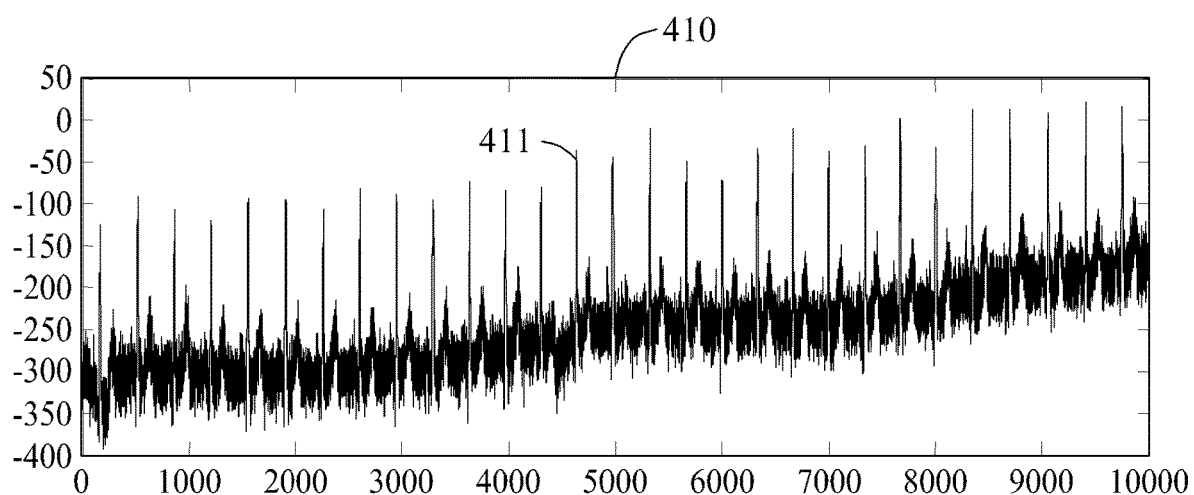
FIG. 4 illustrates an example of aligning an electrocardiogram (ECG) waveform.

FIG. 4 illustrates an example of aligning an ECG waveform.

Referring to FIG. 4, in a graph 410, a horizontal axis represents time and a vertical axis represents an amplitude of the ECG waveform. The graph 410 shows the ECG signal acquired using an ECG sensor. The graph 410 shows a plurality of ECG waveforms 411 in the ECG signal of the same user, and time periods and amplitudes of the ECG waveforms 411 vary depending on a respiration state of the user. When the ECG sensor provides a relatively low performance quality, noise may occur in the ECG waveforms 411. A user authentication apparatus performs preprocessing to eliminate dominant noise from the ECG waveforms so that the ECG waveforms 411 have a form appropriate for a user authentication. For example, the user authentication apparatus extracts an ECG waveform in a range from 0.5 to 40 Hz from the ECG waveforms 411.

Additionally, the user authentication apparatus aligns the ECG waveforms 411 based on an R peak. The user authentication apparatus detects a plurality of R peaks from the ECG waveforms, and aligns the ECG waveforms 411 based on the detected R peaks. The user authentication apparatus performs the user authentication based on the aligned ECG waveforms 411.

Figure 5A:
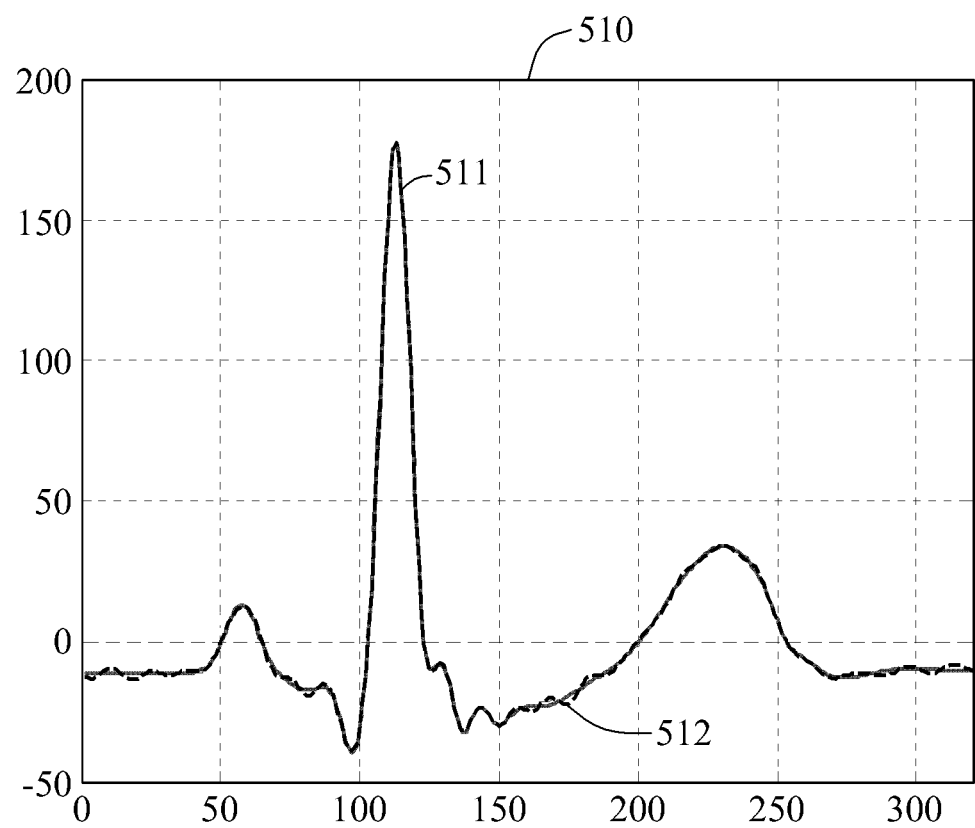
FIGS. 5A and 5B illustrate examples of extracting a predicted ECG waveform.
Figure 5B:
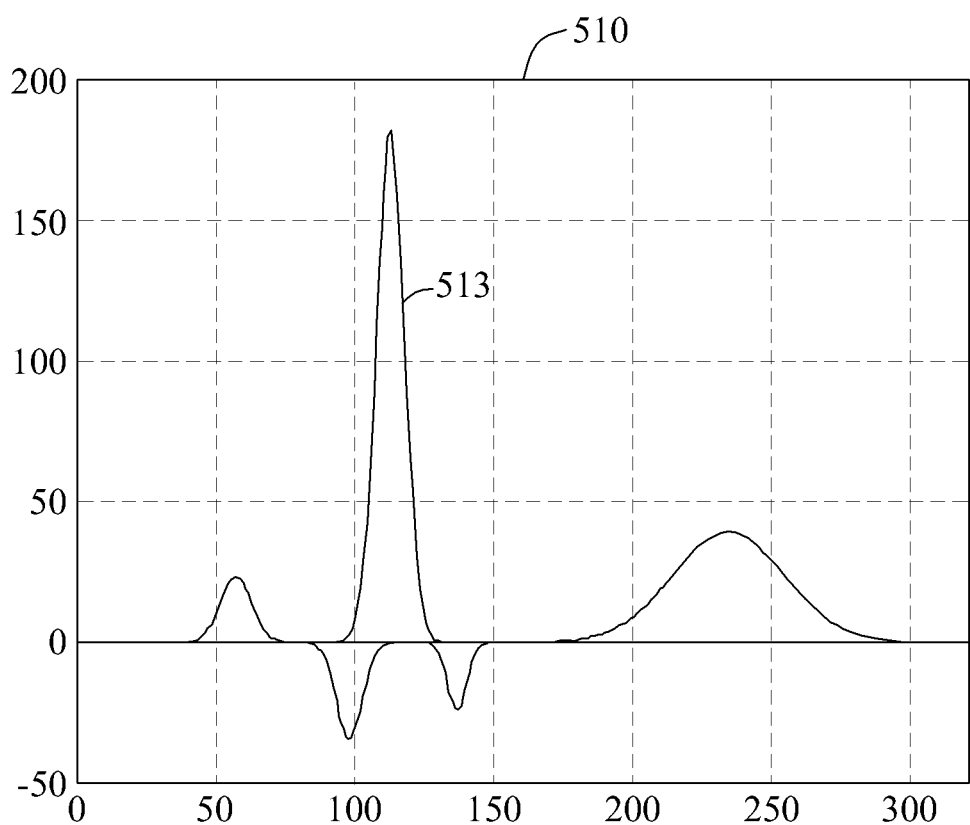

FIGS. 5A and 5B illustrate examples of extracting a predicted ECG waveform 511.

Referring to FIGS. 5A and 5B, horizontal axes represent time and vertical axes represent an amplitude of an ECG waveform in graphs 510 and 520. In a process of pre-registering a user, a user authentication apparatus determines a standard deviation value and an average value of a measured ECG waveform 512, and extracts a plurality of Gaussian functions 513 from the measured ECG waveform 512 based on the standard deviation value and the average value. The user authentication apparatus models the measured ECG waveform 512 using Equation 1 based on the Gaussian functions 513. The user authentication apparatus extracts an amplitude parameter, a duration parameter, and a position parameter using Equation 2.

Additionally, the user authentication apparatus extracts an average heart rate of the user from the measured ECG waveform 512, and extracts an angular velocity parameter from the average heart rate. The user authentication apparatus may extract the predicted ECG waveform 511 by applying the amplitude parameter, the duration parameter, the position parameter, and the angular velocity parameter to the measured ECG waveform 512 using a Kalman filter.

Figure 6:
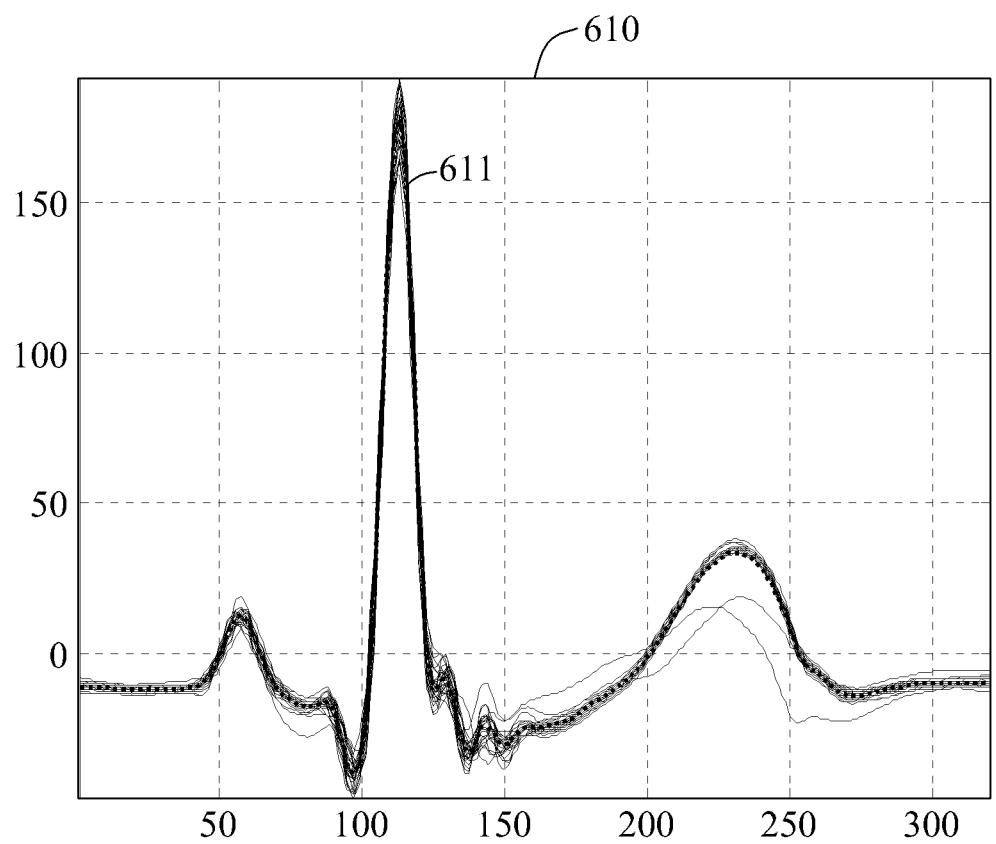
FIG. 6 illustrates an example of filtering an ECG waveform using a Kalman filter.

FIG. 6 illustrates an example of filtering an ECG waveform using a Kalman filter.

Referring to FIG. 6, in a graph 610, a horizontal axis represents time and a vertical axis represents an amplitude of the ECG waveform. A user registration apparatus filters the ECG waveform using the Kalman filter by applying model parameters to the Kalman filter. The model parameters are model parameters extracted from an ECG waveform measured to register a user, and include an amplitude parameter, a duration parameter, a position parameter, and an angular velocity parameter.

The user registration apparatus extracts a predicted registration ECG waveform using the Kalman filter by applying the model parameters to the measured ECG waveform. The user registration apparatus outputs a filtered ECG waveform 611 by combining a predicted ECG waveform and an ECG waveform measured from the user. In this example, a different weight is applied to each of the predicted ECG waveform and the measured ECG waveform.

Figure 7:
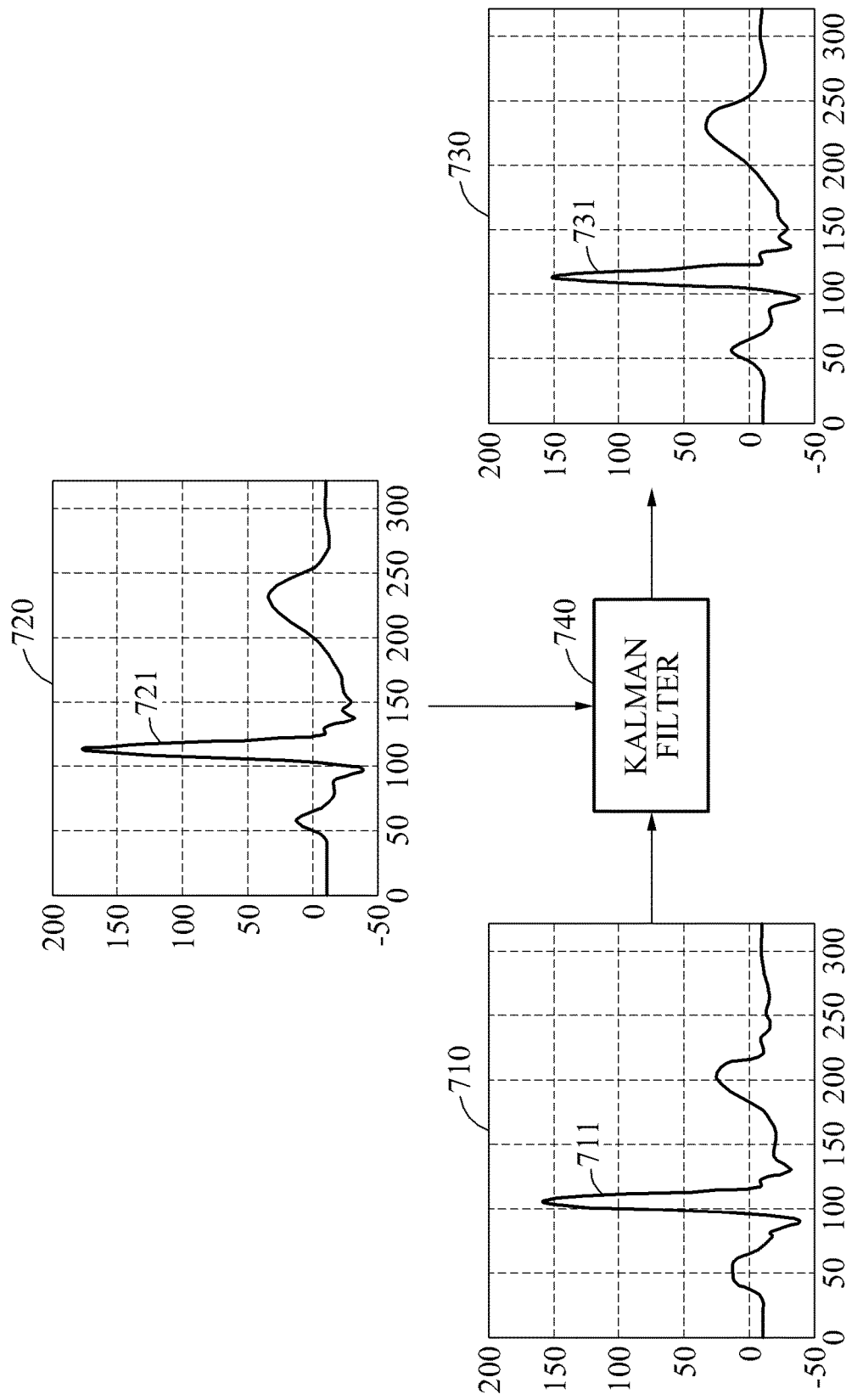
FIG. 7 illustrates an example of a tendency of a distance from an ECG waveform changing through a filtering.

FIG. 7 illustrates an example of a tendency of a distance from an ECG waveform changing through a filtering.

Referring to FIG. 7, in graphs 710, 720, and 730, horizontal axes represent time and vertical axes represent an amplitude of the ECG waveform. In a process of authenticating a user, a user authentication apparatus filters an ECG waveform 711 of the user using a Kalman filter 740 by applying model parameters extracted from an ECG waveform 721 of a pre-registered user to the Kalman filter 740. In this example, the user matches the pre-registered user. The model parameters include an amplitude parameter, a duration parameter, and a position parameter minimizing a distance between the ECG waveform 721 and a sum of a plurality of Gaussian functions extracted from the ECG waveform 721. Also, the model parameters include an angular velocity parameter extracted from the ECG waveform 721.

The model parameters reflects unique characteristics of the ECG waveform 721. When the user of the ECG waveform 711 matches a user of the ECG waveform 721, a prediction error is reduced in the Kalman filter 740. Accordingly, a filtered ECG waveform 731 has a shape close to the shape of the ECG waveform 721 of the pre-registered user.

Figure 8:
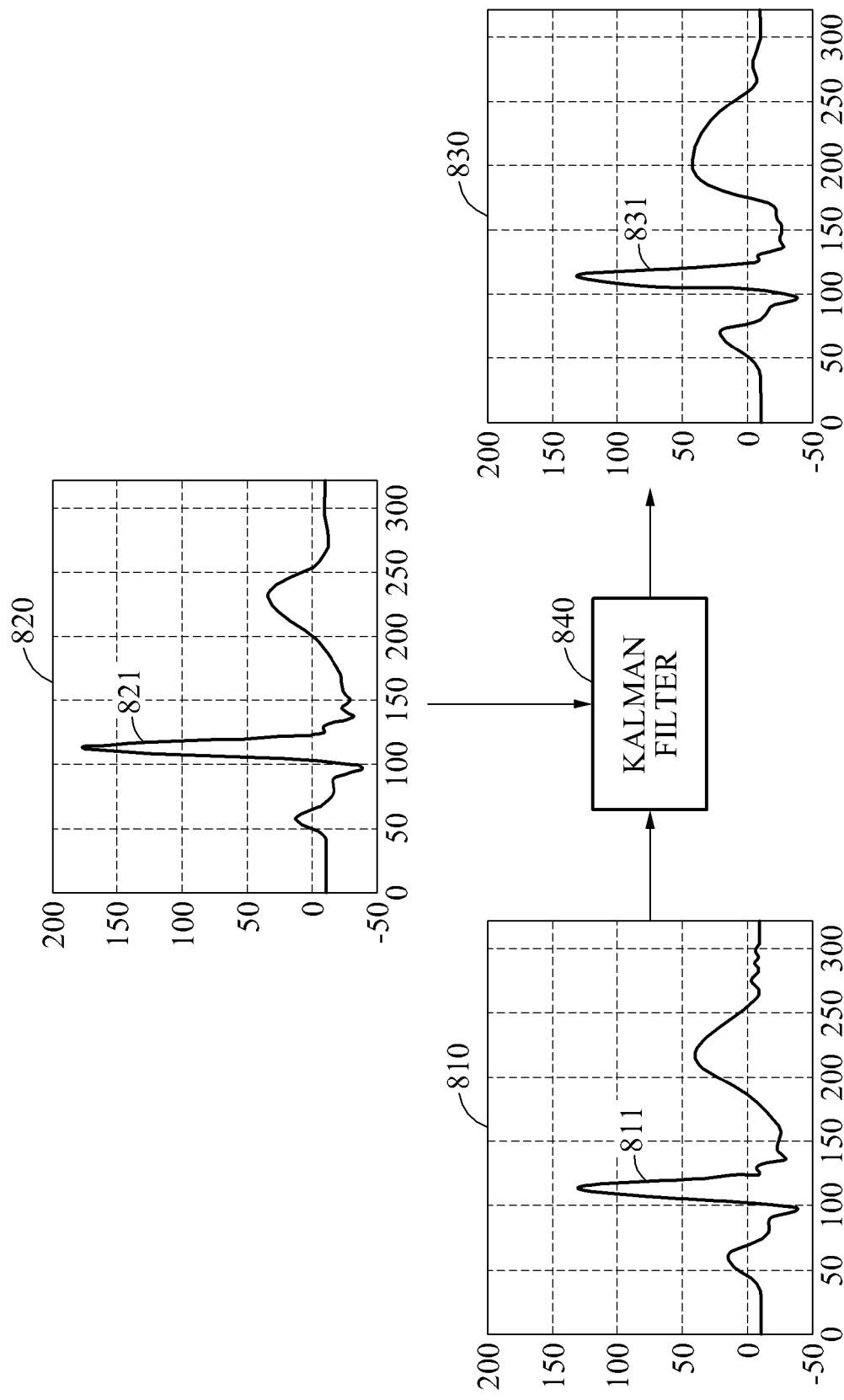
FIG. 8 illustrates another example of a tendency of a distance from an ECG waveform changing through a filtering.

FIG. 8 illustrates another example of a tendency of a distance from an ECG waveform changing through a filtering.

Referring to FIG. 8, in graphs 810, 820, and 830, horizontal axes represent time and vertical axes represent an amplitude of the ECG waveform. In a process of authenticating a user, a user authentication apparatus filters an ECG waveform 811 of the user using a Kalman filter 840 by applying model parameters extracted from an ECG waveform 821 of a pre-registered user to the Kalman filter 840. In this example, the user does not match the pre-registered user. The model parameters an amplitude parameter, a duration parameter, and a position parameter minimizing a distance between the ECG waveform 821 and a sum of a plurality of Gaussian functions extracted from the ECG waveform 821. Also, the model parameters include an angular velocity parameter extracted from the ECG waveform 821.

The model parameter reflects unique characteristics of the ECG waveform 821. When the user of the ECG waveform 811 does not match a user of the ECG waveform 821, a prediction error increases in the Kalman filter 840. Accordingly, a filtered ECG waveform 831 is farther from the ECG waveform 721, and closer to the ECG waveform 811.

Figure 9:
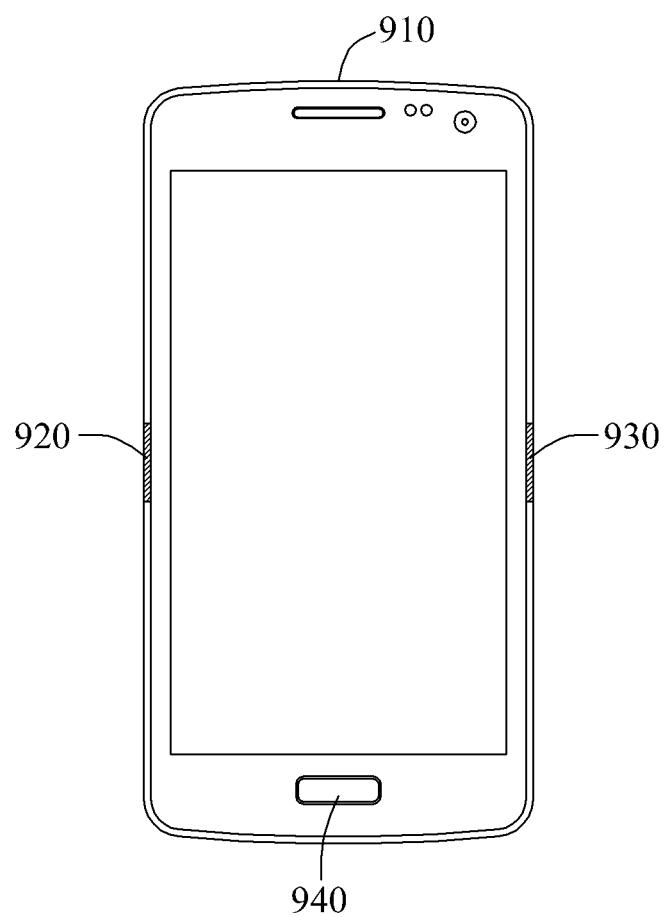
FIG. 9 illustrates another example of a user authentication apparatus.

FIG. 9 illustrates another example of a user authentication apparatus.

Referring to FIG. 9, a mobile terminal 910 includes a positive pole electrode 920, a reference electrode 930, and a negative pole electrode 940 to sense an ECG signal. In the example illustrated in FIG. 9, the positive pole electrode 920 and the reference electrode 930 are disposed on opposite sides of the mobile terminal 910, and the negative pole electrode 940 is disposed in a lower portion of the mobile terminal 910. However, this is merely one example, and as will be apparent to one of ordinary skill in the art, other arrangements of the positive pole electrode 920, the reference electrode 930, and the negative pole electrode 940 are possible.

When fingers of a user contact a plurality of electrodes, for example, the positive pole electrode 920, the reference electrode 930, and the negative pole electrode 940, the mobile terminal 910 senses the ECG signal. The mobile terminal 910 amplifies the ECG signal using an amplifier, and converts the amplified ECG signal into a digital signal. The mobile terminal 910 extracts an ECG waveform from the converted digital signal.

In a process of registering the ECG waveform of the user, the mobile terminal 910 extracts a representative ECG waveform from the ECG waveform of the user being registered based on an R peak, and extracts model parameters by modeling the representative waveform. Also, the mobile terminal 910 filters the ECG waveform extracted from the user being registered using a Kalman filter by applying the model parameters to the Kalman filter, and extracts a plurality of feature points from the filtered ECG waveform.

In a process of authenticating the user, the mobile terminal 910 aligns a plurality of ECG waveforms included in the ECG waveform based on the R peak, and filters the ECG waveform of the user attempting to be authenticated using the Kalman filter by applying model parameters extracted from a pre-registered ECG waveform to the Kalman filter. The mobile terminal 910 compares the filtered ECG waveform and the pre-registered ECG waveform, and determines whether the filtered ECG waveform corresponds to the pre-registered ECG waveform based on a result of the comparing. Based on a result of the determining, the mobile terminal 910 authenticates whether the user is the pre-registered user.

Figure 10:
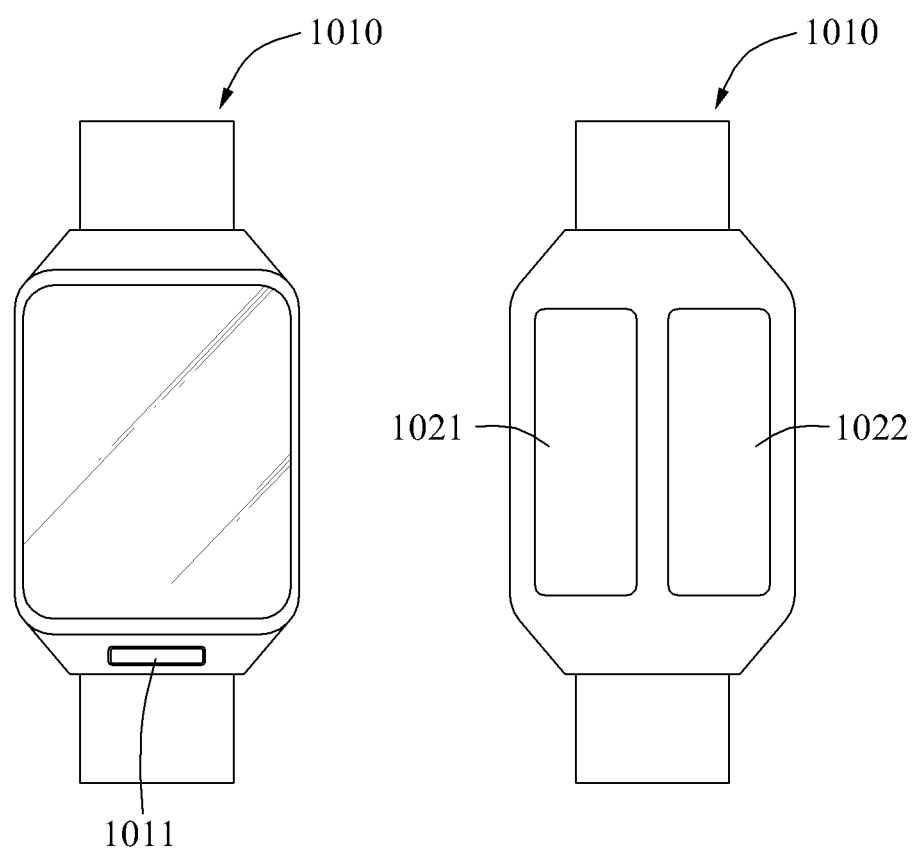
FIG. 10 illustrates another example of a user authentication apparatus.

FIG. 10 illustrates another example of a user authentication apparatus.

Referring to FIG. 10, a wearable terminal 1010 includes a positive pole electrode 1021, a reference electrode 1022, and a negative pole electrode 1011 to sense an ECG signal. In the example illustrated in FIG. 10, the positive pole electrode 1021 and the reference electrode 1022 are disposed on a rear side of the wearable terminal 1010, and the negative pole electrode 1011 is disposed on a front side of the wearable terminal 1010. However, this is merely one example, and as will be apparent to one of ordinary skill in the art, other arrangements of the positive pole electrode 1021, the reference electrode 1022, and the negative pole electrode 1011 are possible.

Similar to the mobile terminal 910 of FIG. 9, the wearable terminal 1010 acquires an ECG signal of a user using a plurality of electrodes, for example, the positive pole electrode 1021, the reference electrode 1022, and the negative pole electrode 1011, extracts an ECG waveform from the ECG signal, and filters the extracted ECG waveform. Also, the wearable terminal 1010 performs the same operations as the mobile terminal 910 in FIG. 9 to register the ECG waveform of the user in advance, or authenticate whether the user matches a pre-registered user.

Figure 11:
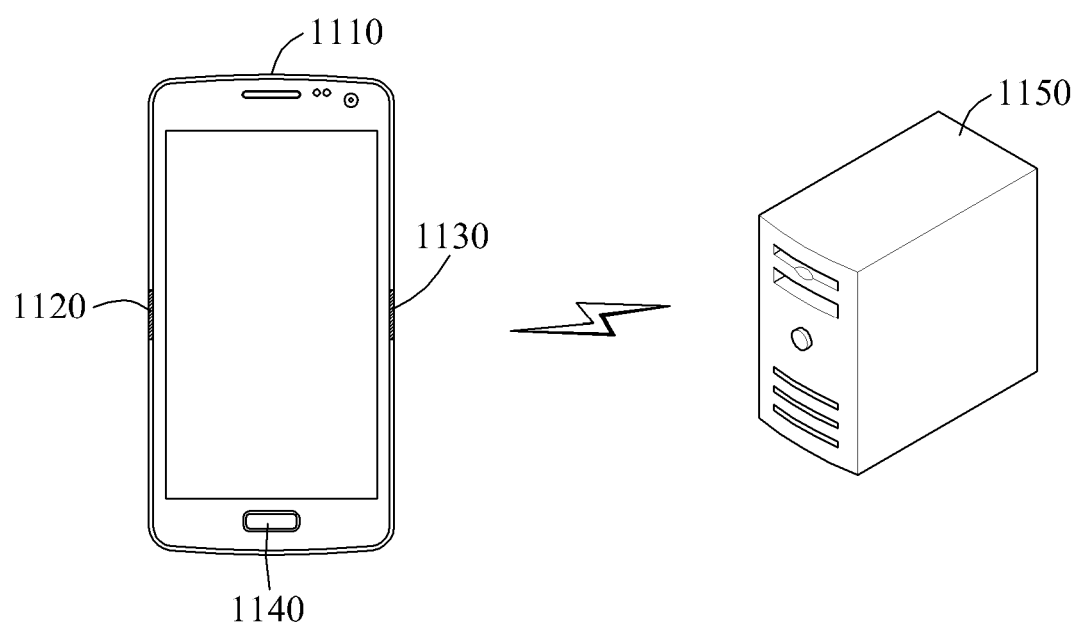
FIG. 11 illustrates another example of a user authentication apparatus.

FIG. 11 illustrates another example of a user authentication apparatus.

Referring to FIG. 11, a mobile terminal 1110 includes a positive pole electrode 1120, a reference electrode 1130, and a negative pole electrode 1140 to sense an ECG signal. In the example in FIG. 11, the positive pole electrode 1120 and the reference electrode 1130 are disposed on both sides of the mobile terminal 1110, and the negative pole electrode 1140 is disposed on a lower portion of the mobile terminal 1110.

However, this is merely one example, and as will be apparent to one of ordinary skill in the art, other arrangements of the positive pole electrode 1120, the reference electrode 1130, and the negative pole electrode 1140 are possible.

The mobile terminal 1110 aligns a plurality of ECG waveforms included in an ECG waveform of a user based on an R peak. Also, the mobile terminal 1110 acquires information on a reference ECG waveform that is an ECG waveform of a pre-registered user from a server 1150. The mobile terminal 1110 receives information on model parameters extracted from the reference ECG waveform from the server 1150. The mobile terminal 1110 filters the ECG waveform of the user using a Kalman filter by applying the model parameters to the Kalman filter. The mobile terminal 1110 extracts a similarity between the reference ECG waveform and the filtered ECG waveform. In one example, the mobile terminal 1110 extracts the similarity based on a plurality of feature points extracted from the reference ECG waveform and a plurality of feature points extracted from the filtered ECG waveform. The mobile terminal 1110 performs authentication as to whether the user matches a pre-registered user based on the similarity. The mobile terminal 1110 may transmit any one or any combination of information on the feature points, information on the similarity, and authentication information on whether the user matches the pre-registered user to the server 1150. In one example, the server 1150 allows the user to access the server 1150 based on the authentication information received from the mobile terminal 1110.

Figure 12:
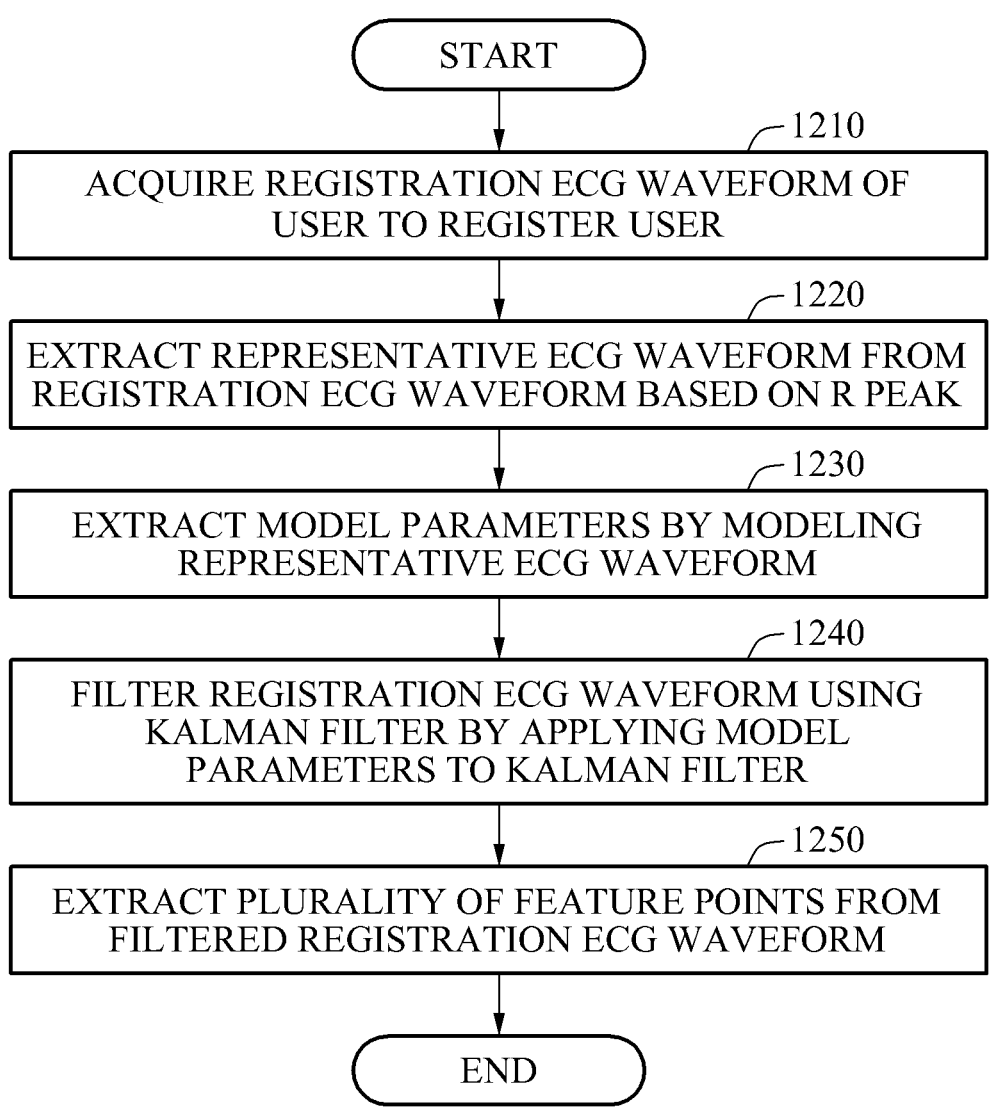
FIG. 12 illustrates an example of a user registration method.

FIG. 12 illustrates an example of a user registration method.

Referring to FIG. 12, in operation 1210, a user registration apparatus acquires a registration ECG waveform of a user to register the user.

In operation 1220, the user registration apparatus extracts a representative ECG waveform from the registration ECG waveform based on an R peak.

In operation 1230, the user registration apparatus extracts model parameters by modeling the representative ECG waveform.

In operation 1240, the user registration apparatus filters the registration ECG waveform using a Kalman filter by applying the model parameters to the Kalman filter.

In operation 1250, the user registration apparatus extracts a plurality of feature points from the filtered registration ECG waveform.

Repeated descriptions with respect to the user registration method of FIG. 12 will be omitted for increased clarity and conciseness because the descriptions provided with reference to FIGS. 1 through 11 are also applicable to the user registration method of FIG. 12.

Figure 13:
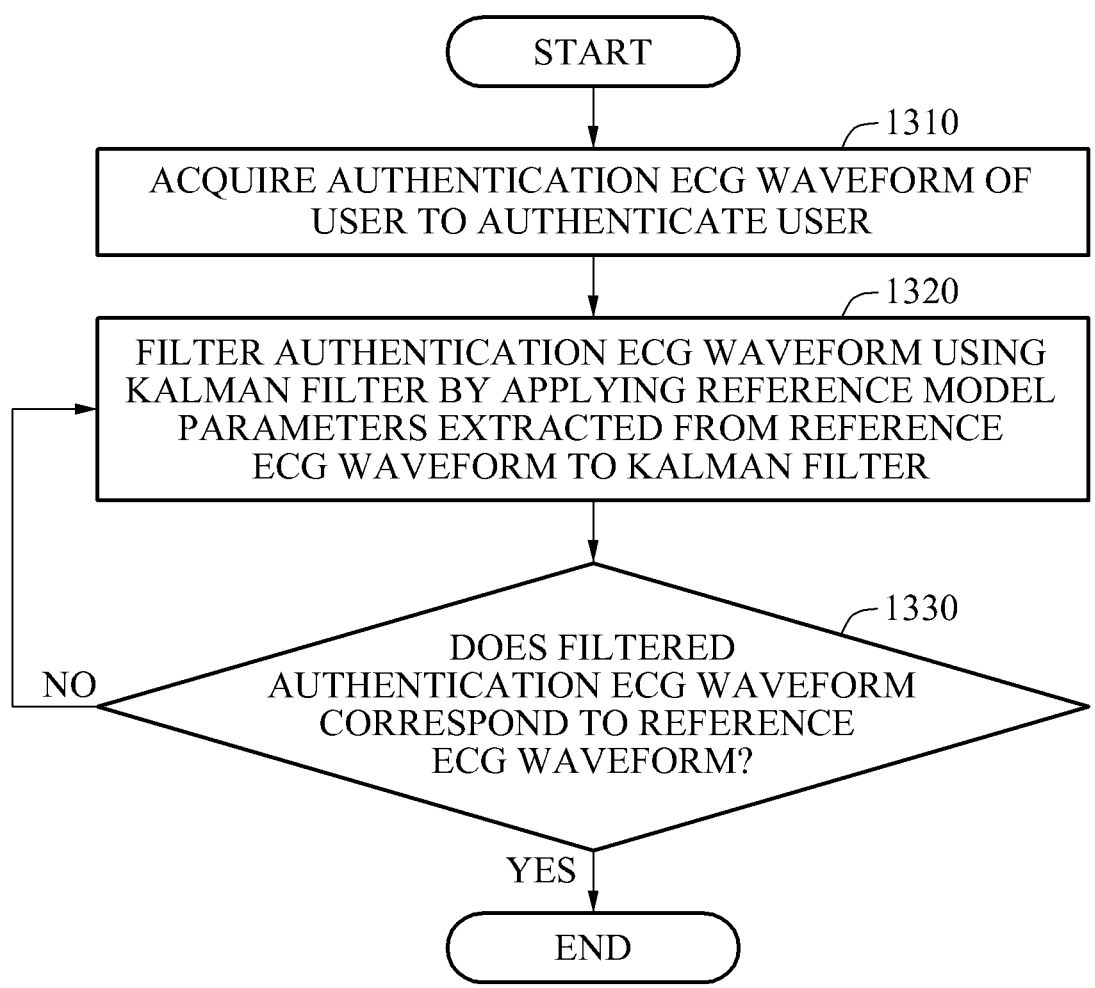
FIG. 13 illustrates an example of a user authentication method.

FIG. 13 illustrates an example of a user authentication method.

Referring to FIG. 13, in operation 1310, a user authentication apparatus acquires an authentication ECG waveform of a user to authenticate the user.

In operation 1320, the user authentication apparatus filters the authentication ECG waveform using a Kalman filter by applying reference model parameters extracted from a reference ECG waveform to the Kalman filter.

In operation 1330, the user authentication apparatus determines whether the filtered authentication ECG waveform corresponds to the reference ECG waveform by comparing the filtered authentication ECG waveform and the reference ECG waveform. In one example, when the filtered authentication ECG waveform does not correspond to the reference ECG waveform, the user authentication apparatus repetitively performs operations 1320 and 1330. In this example, a number of times the operations 1320 and 1330 are repetitively performed may be less than a predetermined threshold.

Repeated descriptions with respect to the user authentication method of FIG. 13 will be omitted for increased clarity and conciseness because the descriptions provided with reference to FIGS. 1 through 11 are also applicable to the user authentication method of FIG. 13.

Figure 14:
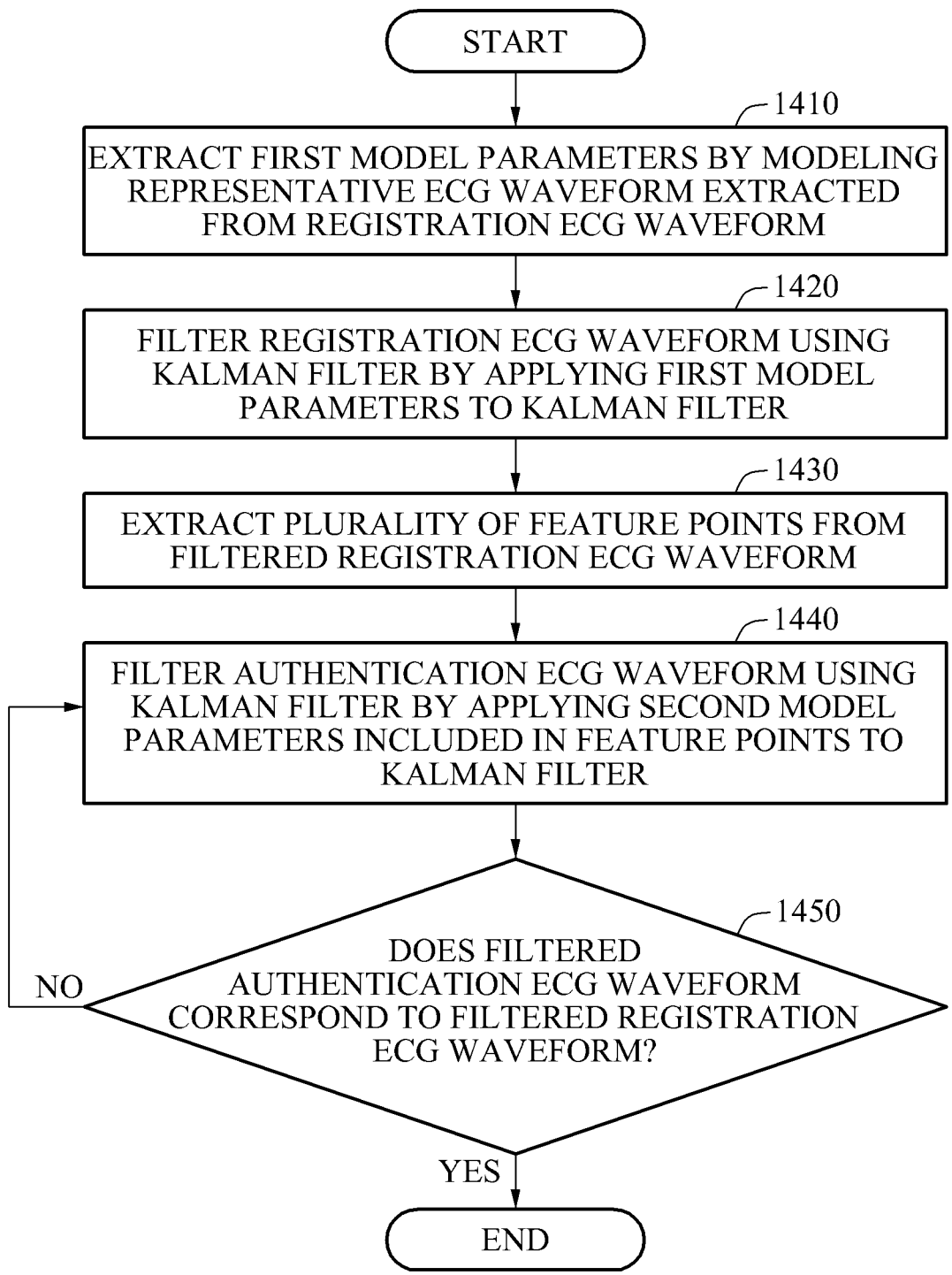
FIG. 14 illustrates another example of a user authentication method.

FIG. 14 illustrates another example of a user authentication method.

Referring to FIG. 14, in operation 1410, a user authentication apparatus extracts first model parameters by modeling a representative ECG waveform extracted from a registration ECG waveform.

In operation 1420, the user authentication apparatus filters the registration ECG waveform using a Kalman filter by applying the first model parameters to the Kalman filter.

In operation 1430, the user authentication apparatus extracts a plurality of feature points from the filtered registration ECG waveform.

In operation 1440, the user authentication apparatus filters an authentication ECG waveform using the Kalman filter by applying second model parameters included in the feature points to the Kalman filter.

In operation 1450, the user authentication apparatus determines whether the filtered authentication ECG waveform corresponds to the filtered registration ECG waveform by comparing the filtered authentication ECG waveform and the filtered registration ECG waveform. In one example, when a second ECG waveform does not correspond to a first ECG waveform, the user authentication apparatus repetitively performs operations 1440 and 1450. In this example, a number of times the operations 1440 and 1450 are repetitively performed may be less than a predetermined threshold.

Repeated descriptions with respect to the user authentication method of FIG. 14 will be omitted for increased clarity and conciseness because the descriptions provided with reference to FIGS. 1 through 11 are also applicable to the user authentication method of FIG. 14.

The ECG waveform acquirer 120, the ECG waveform extractor 130, the model parameter extractor 140, the filter 150, and the feature point extractor 160 in FIG. 1, the ECG waveform acquirer 220, the ECG waveform extractor 230, the filter 240, the feature point extractor 250, and the authenticator 260 in FIG. 2, and the ECG waveform acquirer 320, the ECG waveform extractor 330, the model parameter extractor 341, the filter 342, the feature point extractor 343, the filter 351, the feature point extractor 352, and the user authenticator 353 in FIG. 3, the mobile terminal 910 in FIG. 9, the wearable terminal 1010 in FIG. 10, and the mobile terminal 1110 and the server 1150 in FIG. 11 that perform the various operations described with respect to FIGS. 1-14 are implemented by hardware components. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, controllers, generators, drivers, memories, comparators, arithmetic logic units, adders, multipliers, and any other electronic components known to one of ordinary skill in the art. In one example, the hardware components are implemented by computing hardware, for example, by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 1-14. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 12-14 that perform the operations described herein with respect to FIGS. 1-14 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. For example, suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A user authentication apparatus, comprising:
a processor configured to:
    acquire an authentication electrocardiogram (ECG) waveform;
    filter the authentication ECG waveform using a Kalman filter by applying a reference model parameter extracted from a reference ECG waveform to the Kalman filter;
    extract a plurality of feature points from the filtered authentication ECG waveform;
    determine a distance between the extracted feature points and a plurality of feature points of the reference ECG waveform;
    in response to a similarity corresponding to the determined distance being greater than a predetermined threshold, determine the filtered authentication ECG waveform as corresponding to the reference ECG waveform; and
    authenticate a user of the authentication ECG waveform as being a user of the reference ECG waveform,
wherein the determined distance is associated with a prediction error in the Kalman filter, and
wherein the prediction error is reduced when the user of the authentication ECG waveform is the same as the user of the reference ECG waveform, and the prediction error increases when the user of the authentication ECG waveform is not the user of the reference ECG waveform.

2. The apparatus of claim 1, wherein the reference model parameter comprises any one or any combination of any two or more of a first amplitude parameter indicating an amplitude for each of a plurality of first Gaussian functions extracted from the reference ECG waveform, a first duration parameter indicating a duration for each of the first Gaussian functions, a first position parameter indicating a position for each of the first Gaussian functions, and a first angular velocity parameter indicating an angular velocity based on a change in a phase of the reference ECG waveform.

3. The apparatus of claim 2, wherein the processor is further configured to extract a predicted authentication ECG waveform by applying the reference model parameter to the authentication ECG waveform using the Kalman filter, and output the filtered authentication ECG waveform by combining the authentication ECG waveform and the predicted authentication ECG waveform.

4. The apparatus of claim 1, wherein the processor is further configured to extract a plurality of second Gaussian functions from the filtered authentication ECG waveform, and extract any one or any combination of any two or more of a second amplitude parameter indicating an amplitude for each of the second Gaussian functions, a second duration parameter indicating a duration for each of the second Gaussian functions, and a second position parameter indicating a position for each of the second Gaussian functions so that a distance between the filtered authentication ECG waveform and a sum of the second Gaussian functions is minimized.

5. The apparatus of claim 4, wherein the processor is further configured to determine the similarity based on any one or any combination of any two or more of a distance between the first amplitude parameter and the second amplitude parameter, a distance between the first duration parameter and the second duration parameter, and a distance between the first position parameter and the second position parameter.

6. The apparatus of claim 5, wherein the processor is further configured to determine the similarity by applying a weight to each of the distance between the first amplitude parameter and the second amplitude parameter, the distance between the first duration parameter and the second duration parameter, and the distance between the first position parameter and the second position parameter.

7. The apparatus of claim 1, wherein the processor is further configured to operate repetitively, in response to determining that the filtered authentication ECG waveform does not correspond to the reference ECG waveform.

8. The apparatus of claim 7, wherein the processor is further configured to determine that the user of the authentication ECG waveform is not the user of the reference ECG waveform, in response to a number of operations repetitively performed by the processor being greater than another predetermined threshold.

9. The apparatus of claim 7, wherein
the processor is further configured to authenticate the user of the authentication ECG waveform as being the user of the reference ECG waveform, in response to the similarity being greater than the predetermined threshold and increasing as operations are repetitively performed by the processor.

10. The apparatus of claim 1, wherein the processor is further configured to extract as the feature points from the filtered authentication ECG waveform any one or any combination of any two or more of a PR interval, a PR segment, a QRS complex, an ST segment, an ST interval, a QT interval, an RR interval, an amplitude, a position, a noise power, and a predetermined statistical value of the filtered authentication ECG waveform.

11. The apparatus of claim 1, wherein the processor is further configured to reset a variable of the Kalman filter in response to determining that the user of the authentication ECG waveform is not the user of the reference ECG waveform.

12. The apparatus of claim 1, wherein the processor is further configured to eliminate a motion artifact from the ECG waveform before the filtering of the authentication ECG waveform with the Kalman filter that has been applied the reference model parameter extracted from the reference ECG waveform.

13. A user registration apparatus, comprising:
a processor configured to:
acquire a registration electrocardiogram (ECG) waveform;
extract a representative ECG waveform from the registration ECG waveform based on an R peak;
determine a standard deviation value of the representative ECG waveform;
extract a first model parameter by modeling the representative ECG waveform based on the standard deviation value;
filter the registration ECG waveform using a Kalman filter by applying the first model parameter to the Kalman filter;
store the filtered registration ECG waveform as a reference ECG waveform; and
extract a plurality of feature points from the filtered registration ECG waveform,
wherein a prediction error is reduced in the Kalman filter when a user of an authentication ECG waveform is the same as a user of the reference ECG waveform, and the prediction error increases when the user of the authentication ECG waveform is not the user of the reference ECG waveform,
wherein a distance is determined between extracted feature points of the authentication ECG waveform and the plurality of feature points from the filtered registration ECG waveform,
wherein, in response to a similarity corresponding to the determined distance being greater than a predetermined threshold, the filtered authentication ECG waveform is determined as corresponding to the reference ECG waveform, and
wherein the user of the authentication ECG waveform is authenticated as being the user of the reference ECG waveform.

14. The apparatus of claim 13, wherein the processor is further configured to extract first Gaussian functions from the representative ECG waveform, and extract any one or any combination of any two or more of a first amplitude parameter indicating an amplitude for each of the first Gaussian functions, a first duration parameter indicating a duration for each of the first Gaussian functions, and a first position parameter for each of the first Gaussian functions so that a distance between the representative ECG waveform and a sum of the first Gaussian functions is minimized.

15. The apparatus of claim 14, wherein the processor is further configured to extract second Gaussian functions from the filtered registration ECG waveform, and extract any one or any combination of any two or more of a second amplitude parameter indicating an amplitude for each of the second Gaussian functions, a second duration parameter indicating a duration for each of the second Gaussian functions, and a second position parameter indicating a position for each of the second Gaussian functions so that a distance between the filtered registration ECG waveform and a sum of the second Gaussian functions is minimized.

16. The apparatus of claim 13, wherein the processor is further configured to extract a predicted registration ECG waveform by applying the first model parameter to the registration ECG waveform based on Gaussian functions using the Kalman filter, and output the filtered registration ECG waveform by combining the registration ECG waveform and the predicted registration ECG waveform.

17. The apparatus of claim 13, wherein the processor is further configured to extract as the feature points from the filtered registration ECG waveform any one or any combination of any two or more of a PR interval, a PR segment, a QRS complex, an ST segment, an ST interval, a QT interval, an RR interval, an amplitude, a position, a noise power, and a predetermined statistic value of the filtered registration ECG waveform.

18. The apparatus of claim 13, wherein the processor is further configured to eliminate a motion artifact from the registration ECG waveform before the filtering of the registration ECG waveform with the Kalman filter that has been applied the first model parameter.

19. A user authentication apparatus, comprising:
a processor configured to:
    extract a first model parameter by modeling a representative electrocardiogram (ECG) waveform extracted from a registration ECG waveform;
    filter the registration ECG waveform using a Kalman filter by applying the first model parameter to the Kalman filter;
    extract a plurality of feature points from the filtered registration ECG waveform;
    filter an authentication ECG waveform using the Kalman filter by applying a second model parameter included in the feature points from the filtered registration ECG waveform to the Kalman filter;
    extract a plurality of feature points from the filtered authentication ECG waveform;
    determine a distance between the extracted feature points from the filtered authentication ECG waveform and the extracted feature points from the filtered registration ECG waveform; and
    in response to a similarity corresponding to the determined distance being greater than a predetermined threshold, determine the filtered authentication ECG waveform as corresponding to the registration ECG waveform, and authenticate a user of the authentication ECG waveform as being a user of the registration ECG waveform,
wherein the determined distance is associated with a prediction error in the Kalman filter, and
wherein the prediction error is reduced when the user of the authentication ECG waveform is the same as the user of the registration ECG waveform, and the prediction error increases when the user of the authentication ECG waveform is not the user of the registration ECG waveform.

20. A user authentication method, comprising:
acquiring an authentication electrocardiogram (ECG) waveform;
filtering the authentication ECG waveform using a Kalman filter by applying a reference model parameter extracted from a reference ECG waveform to the Kalman filter;
extracting a plurality of feature points from the filtered authentication ECG waveform;
determining a distance between the extracted feature points and a plurality of feature points of the reference ECG waveform;
in response to a similarity corresponding to the determined distance being greater than a predetermined threshold, determining the filtered authentication ECG waveform as corresponding to a registration ECG waveform; and
authenticating a user of the authentication ECG waveform as being a user of the registration ECG waveform,
wherein the determined distance is associated with a prediction error in the Kalman filter, and
wherein the prediction error is reduced when the user of the authentication ECG waveform is the same as the user of the reference ECG waveform, and the prediction error increases when the user of the authentication ECG waveform is not the user of the reference ECG waveform.

21. A user registration method, comprising:
acquiring a registration electrocardiogram (ECG) waveform;
extracting a representative ECG waveform from the registration ECG waveform based on an R peak;
determining a standard deviation value of the representative ECG waveform;
extracting a model parameter by modeling the representative ECG waveform based on the standard deviation value;
filtering the registration ECG waveform using a Kalman filter by applying the model parameter to the Kalman filter;
storing the filtered registration ECG waveform as a reference ECG waveform; and
extracting a plurality of feature points from the filtered registration ECG waveform,
wherein a prediction error is reduced in the Kalman filter when a user of an authentication ECG waveform is the same as a user of the reference ECG waveform, and the prediction error increases when the user of the authentication ECG waveform is not the user of the reference ECG waveform,
wherein a distance is determined between extracted feature points from the authentication ECG waveform and the plurality of feature points from the filtered registration ECG waveform, and
wherein, in response to a similarity corresponding to the determined distance being greater than a predetermined threshold, the filtered authentication ECG waveform is determined as corresponding to the reference ECG waveform and the user of the authentication ECG waveform is authenticated as being the user of the reference ECG waveform.

22. A user authentication method, comprising:
extracting a first model parameter by modeling a representative electrocardiogram (ECG) waveform extracted from a registration ECG waveform;
filtering the registration ECG waveform using a Kalman filter by applying the first model parameter to the Kalman filter;
extracting a plurality of feature points from the filtered registration ECG waveform;
filtering an authentication ECG waveform using the Kalman filter by applying a second model parameter included in the feature points from the filtered registration ECG waveform to the Kalman filter;
extracting a plurality of feature points from the filtered authentication ECG waveform;
determining a distance between the extracted feature points from the filtered authentication ECG waveform and the extracted feature points from the filtered registration ECG waveform; and in response to a similarity corresponding to the determined distance being greater than a predetermined threshold, determining the filtered authentication ECG waveform as corresponding to the registration ECG waveform; and authenticating a user of the authentication ECG waveform as being a user of the registration ECG waveform, wherein the determined distance is associated with a prediction error in the Kalman filter, and wherein the prediction error is reduced when the user of the authentication ECG waveform is the same as the user of the registration ECG waveform, and the prediction error increases when the user of the authentication ECG waveform is not the user of the registration ECG waveform.

23. A user authentication method, comprising:

acquiring an authentication electrocardiogram (ECG) waveform of a user to be authenticated;

filtering the authentication ECG waveform using a Kalman filter adjusted based on a characteristic extracted from a reference ECG waveform of a pre-registered user;

extracting a plurality of feature points from the filtered authentication ECG waveform;

determining a distance between the extracted feature points and a plurality of feature points of the reference ECG waveform;

in response to a similarity corresponding to the determined distance being greater than a predetermined threshold, determining the filtered authentication ECG waveform as corresponding to the reference ECG waveform; and authenticating the user to be authenticated as being the pre-registered user, wherein the determined distance is associated with a prediction error in the Kalman filter, and wherein the prediction error is reduced when the user to be authenticated is the same as the pre-registered user, and the prediction error increases when the user to be authenticated is not the pre-registered user.

24. The method of claim 23, wherein the characteristic is a parameter of a Gaussian function modeling the reference ECG waveform.

* * * * *